United States Patent
Fujikura et al.

(10) Patent No.: US 9,433,759 B2
(45) Date of Patent: Sep. 6, 2016

(54) INSERTION ASSISTING TOOL FOR ENDOSCOPE

(75) Inventors: Tetsuya Fujikura, Saitama (JP); Hirotaka Kawano, Saitama (JP)

(73) Assignee: FUJIFILM CORPORATION, Tokyo (JP)

( * ) Notice: Subject to any disclaimer, the term of this patent is extended or adjusted under 35 U.S.C. 154(b) by 641 days.

(21) Appl. No.: 13/476,174

(22) Filed: May 21, 2012

(65) Prior Publication Data
US 2012/0232347 A1 Sep. 13, 2012

Related U.S. Application Data

(60) Continuation of application No. 11/892,615, filed on Aug. 24, 2007, now abandoned, which is a division of application No. 11/001,181, filed on Dec. 2, 2004, now Pat. No. 8,088,063.

(30) Foreign Application Priority Data

Dec. 5, 2003 (JP) ................................. 2003-407979
Dec. 9, 2003 (JP) ................................. 2003-410641
Mar. 29, 2004 (JP) ................................. 2004-96451
Nov. 5, 2004 (JP) ................................. 2004-322795

(51) Int. Cl.
*A61B 1/04* (2006.01)
*A61M 25/06* (2006.01)
*A61B 17/34* (2006.01)
*A61M 25/10* (2013.01)

(52) U.S. Cl.
CPC ...... *A61M 25/0662* (2013.01); *A61B 17/3415* (2013.01); *A61B 17/3417* (2013.01); *A61B 17/3431* (2013.01); *A61M 25/10* (2013.01)

(58) Field of Classification Search
USPC .................. 600/104, 113–114, 121–123, 129
See application file for complete search history.

(56) References Cited

U.S. PATENT DOCUMENTS

| | | | |
|---|---|---|---|
| 4,040,413 A | | 8/1977 | Ohshiro |
| 4,062,363 A | * | 12/1977 | Bonner, Jr. ........ A61M 25/0111 604/171 |
| 4,327,735 A | * | 5/1982 | Hampson ........... A61M 25/0111 604/171 |
| 4,515,592 A | * | 5/1985 | Frankhouser ...... A61M 25/0111 604/163 |
| 4,543,090 A | * | 9/1985 | McCoy ............. A61M 25/0158 600/151 |

(Continued)

FOREIGN PATENT DOCUMENTS

| | | |
|---|---|---|
| EP | 0 138 089 | 4/1985 |
| JP | 10-248794 | 9/1998 |

(Continued)

OTHER PUBLICATIONS

European Search Report from European patent application No. 04028767.4 dated Apr. 18, 2006.

(Continued)

*Primary Examiner* — Matthew J Kasztejna
(74) *Attorney, Agent, or Firm* — Harness, Dickey & Pierce, P.L.C.

(57) ABSTRACT

An insertion assisting tool for an endoscope into which an insertion section of the endoscope is inserted from a base end portion side. The insertion assisting tool may include a fluid sealing device which seals a space between a base end part of the insertion assisting tool and the endoscope insertion section, the space being formed while the insertion section of the endoscope is inserted into the base end portion side.

5 Claims, 23 Drawing Sheets

(56) References Cited

U.S. PATENT DOCUMENTS

| | | | | |
|---|---|---|---|---|
| 4,619,247 | A * | 10/1986 | Inoue | A61B 1/00082 600/116 |
| 4,809,678 | A * | 3/1989 | Klein | A61B 1/00142 600/121 |
| 4,875,468 | A * | 10/1989 | Krauter | A61B 1/015 128/DIG. 14 |
| 5,054,821 | A * | 10/1991 | Hillstead | B25B 27/0028 285/244 |
| 5,087,246 | A | 2/1992 | Smith | |
| RE33,854 | E * | 3/1992 | Adair | A61B 1/00101 600/109 |
| 5,104,389 | A | 4/1992 | Deem et al. | |
| 5,168,863 | A * | 12/1992 | Kurtzer | A61B 1/00142 206/363 |
| 5,237,984 | A * | 8/1993 | Williams, III | A61B 1/00142 359/510 |
| 5,301,657 | A * | 4/1994 | Lafferty | A61B 1/00096 206/438 |
| 5,334,166 | A | 8/1994 | Palestrant | |
| 5,389,080 | A | 2/1995 | Yoon | |
| 5,423,848 | A * | 6/1995 | Washizuka | A61B 17/34 604/164.11 |
| 5,429,609 | A | 7/1995 | Yoon | |
| 5,454,364 | A * | 10/1995 | Kruger | A61B 1/00082 600/114 |
| 5,458,132 | A * | 10/1995 | Yabe | A61B 1/00142 600/121 |
| 5,468,248 | A | 11/1995 | Chin et al. | |
| 5,492,304 | A * | 2/1996 | Smith | A61B 17/3462 251/149.1 |
| 5,496,259 | A * | 3/1996 | Perkins | A61B 1/05 600/121 |
| 5,509,908 | A | 4/1996 | Hillstead et al. | |
| 5,556,367 | A | 9/1996 | Yabe et al. | |
| 5,569,161 | A | 10/1996 | Ebling et al. | |
| 5,599,305 | A | 2/1997 | Hermann et al. | |
| 5,607,391 | A | 3/1997 | Klinger et al. | |
| 5,669,881 | A | 9/1997 | Dunshee | |
| 5,695,449 | A * | 12/1997 | Moriyama | A61B 1/00142 600/121 |
| 5,715,815 | A * | 2/1998 | Lorenzen | A61M 16/0463 128/205.12 |
| 5,779,624 | A | 7/1998 | Chang | |
| 5,792,045 | A * | 8/1998 | Adair | A61B 1/042 600/122 |
| 5,842,971 | A * | 12/1998 | Yoon | 600/144 |
| 5,876,328 | A * | 3/1999 | Fox | A61B 19/081 600/121 |
| 5,904,147 | A * | 5/1999 | Conlan | A61M 25/0108 128/899 |
| 6,302,873 | B1 | 10/2001 | Moenning | |
| 6,558,379 | B1 * | 5/2003 | Batchelor et al. | 606/41 |
| 7,105,009 | B2 | 9/2006 | Johnson et al. | |
| 7,553,297 | B2 | 6/2009 | Lajtai et al. | |
| 8,088,063 | B2 * | 1/2012 | Fujikura | A61B 17/3415 600/101 |
| 8,647,261 | B2 * | 2/2014 | Jaworek | A61M 25/0111 600/114 |
| 2002/0022762 | A1 | 2/2002 | Beane et al. | |
| 2002/0029037 | A1 | 3/2002 | Kim | |
| 2002/0128604 | A1 | 9/2002 | Nakajima | |
| 2002/0147385 | A1 * | 10/2002 | Butler et al. | 600/114 |
| 2003/0216615 | A1 * | 11/2003 | Ouchi | 600/121 |
| 2005/0119613 | A1 | 6/2005 | Moenning et al. | |

FOREIGN PATENT DOCUMENTS

| | | |
|---|---|---|
| JP | 2000-126121 | 5/2000 |
| JP | 2001-340462 | 12/2001 |
| JP | 2002-301019 | 10/2002 |
| WO | WO 98/13083 | 4/1998 |

OTHER PUBLICATIONS

Partial European Search Report dated Apr. 11, 2005.
Office Action for U.S. Appl. No. 11/001,181 dated Mar. 12, 2010.
Office Action for U.S. Appl. No. 11/001,181 dated Nov. 23, 2010.
Office Action for U.S. Appl. No. 11/001,181 dated Apr. 12, 2011.
Notice of Allowance for U.S. Appl. No. 11/001,181 dated Aug. 29, 2011.

* cited by examiner

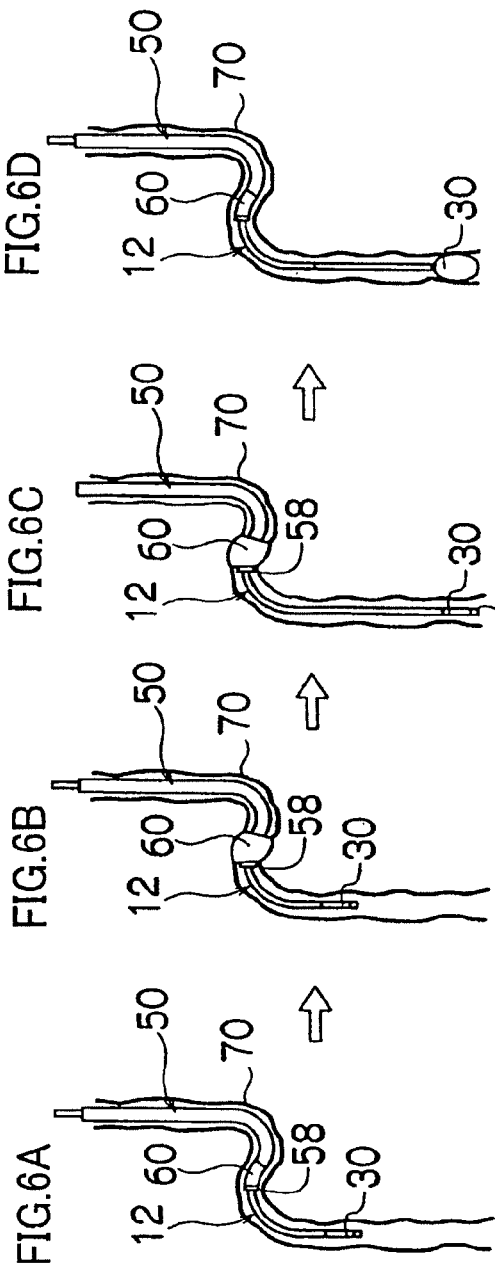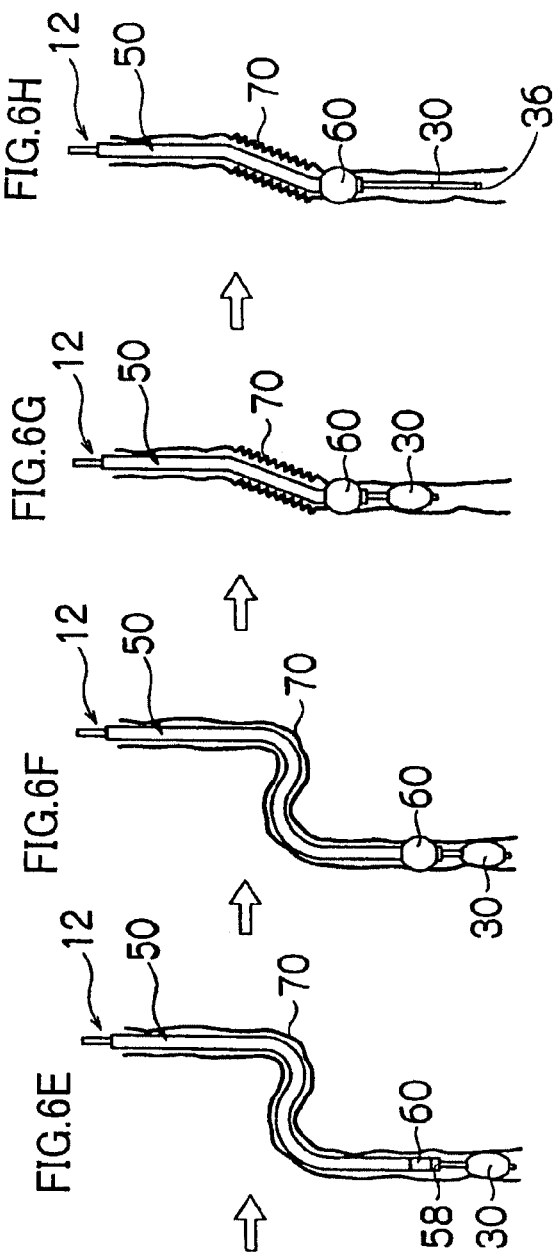

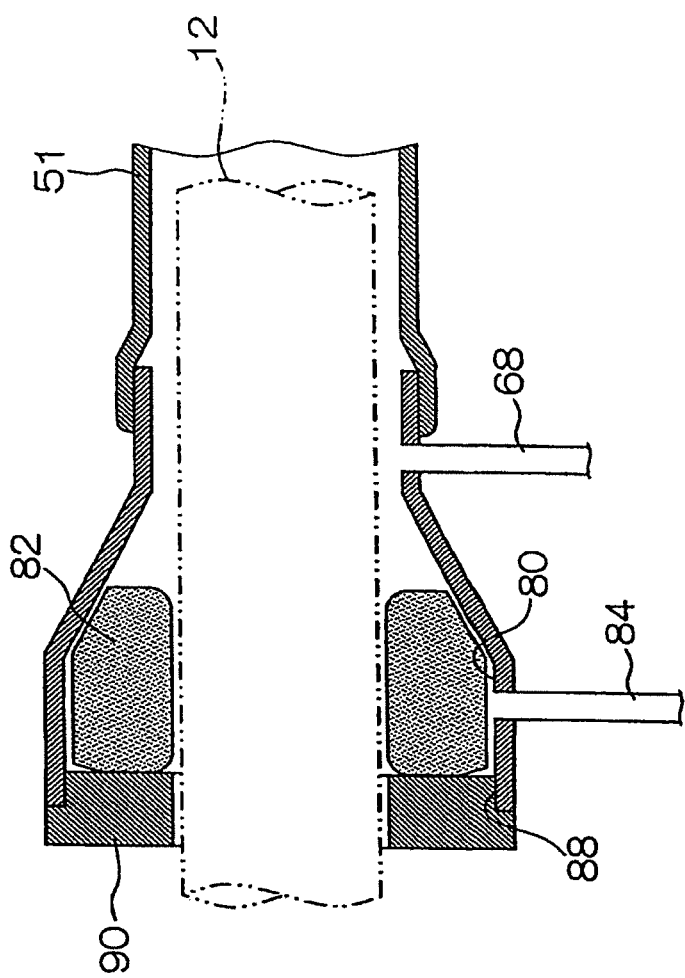

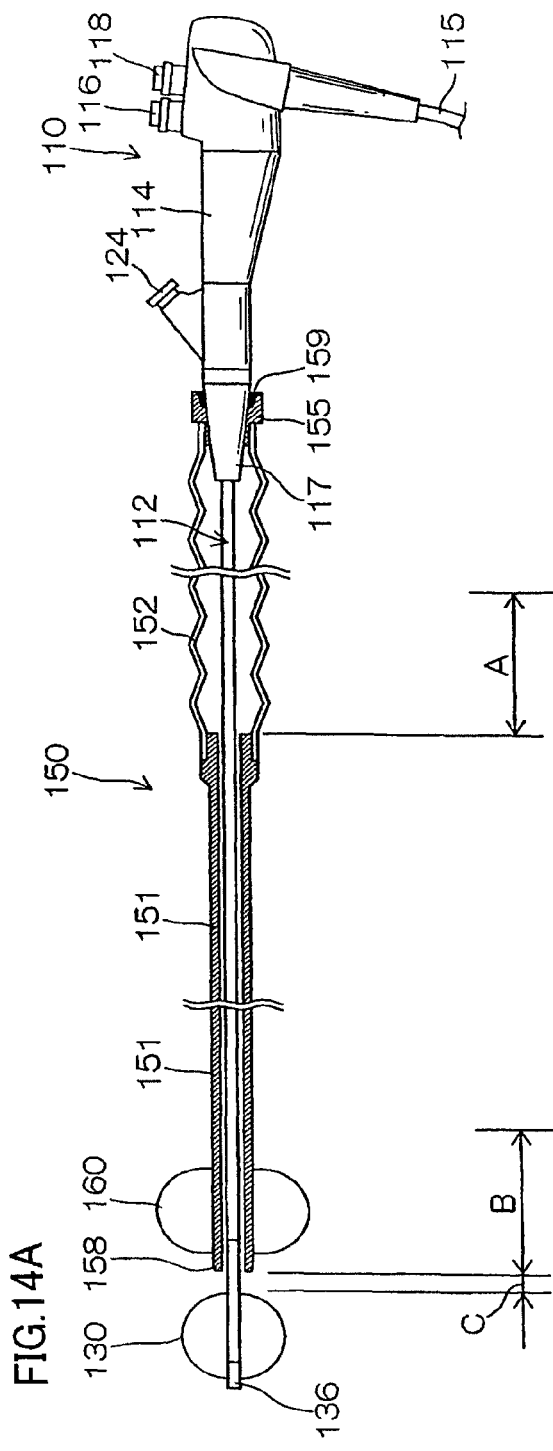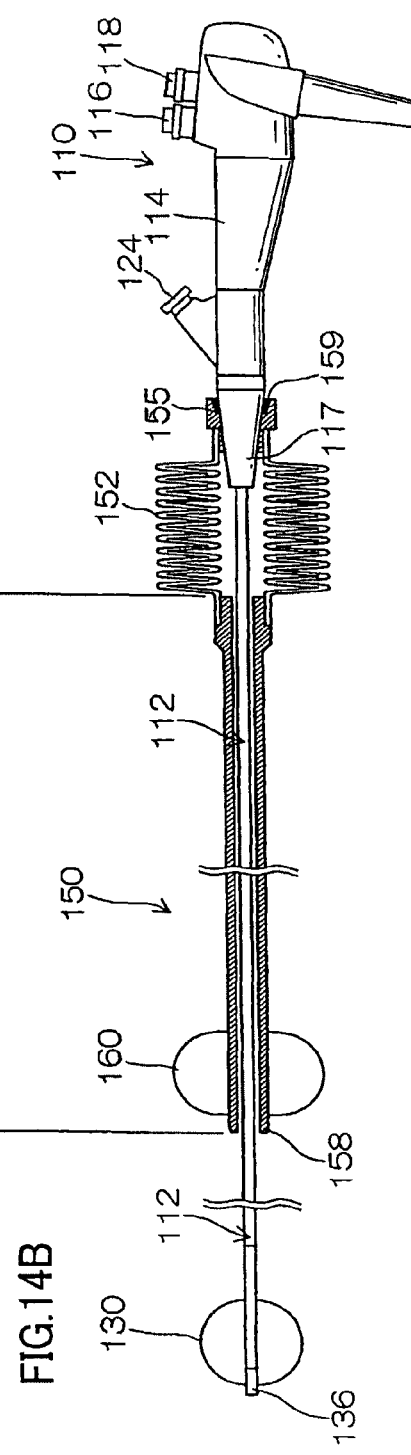
FIG.14A
FIG.14B

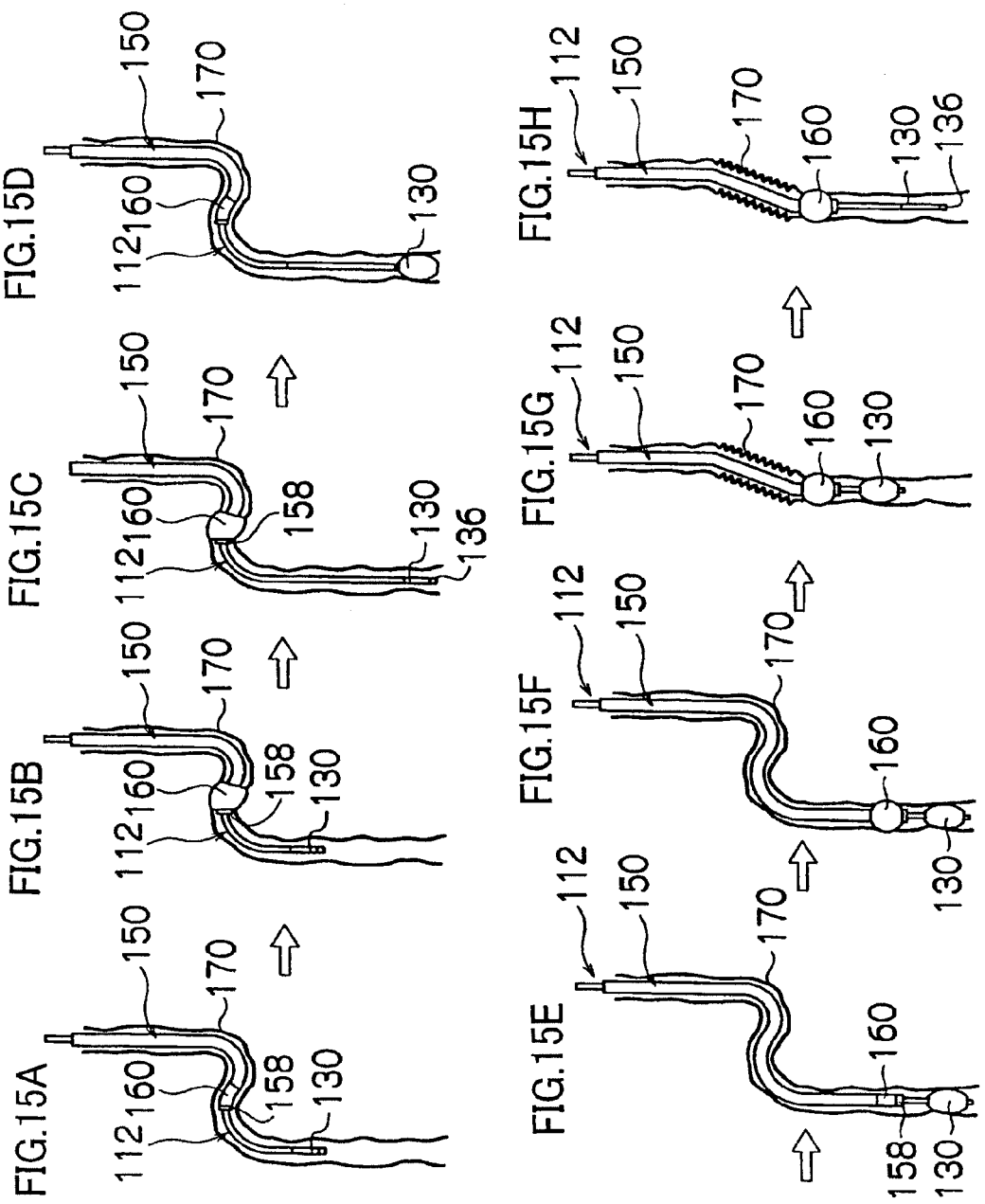

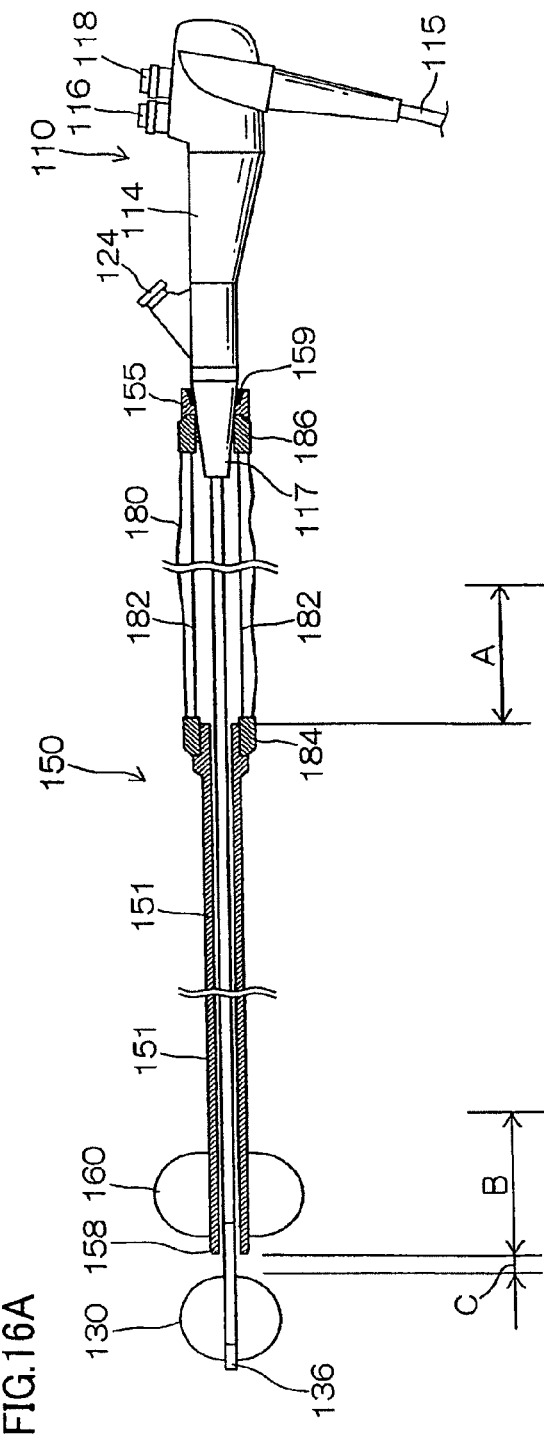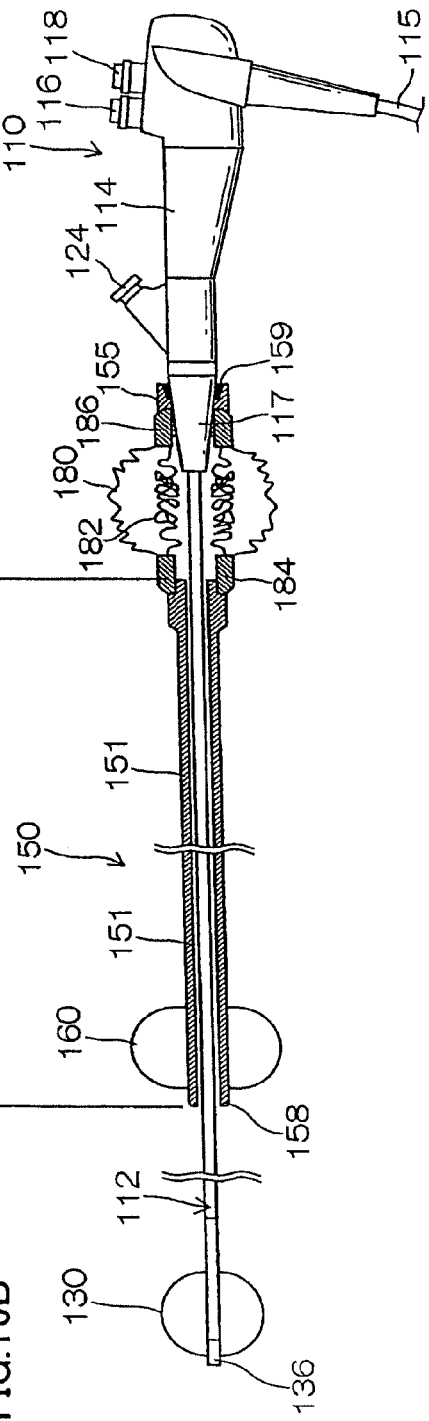
FIG. 16A
FIG. 16B

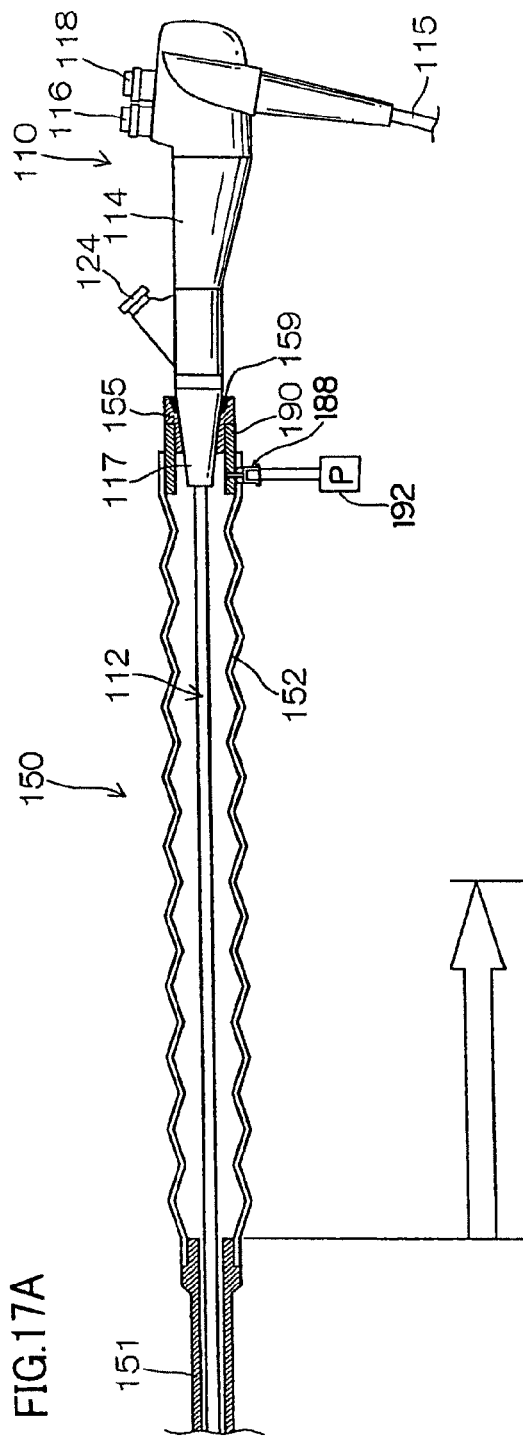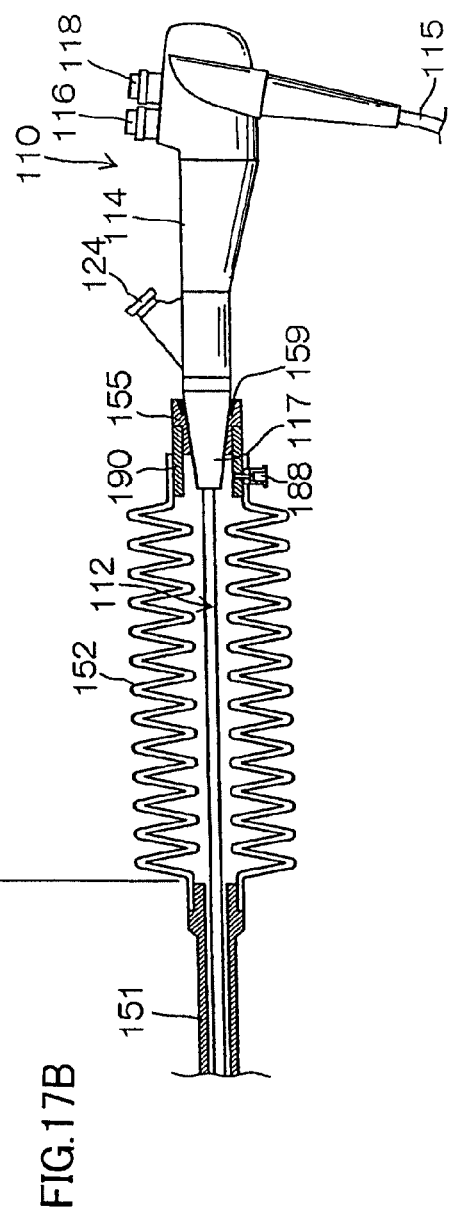
FIG.17A
FIG.17B

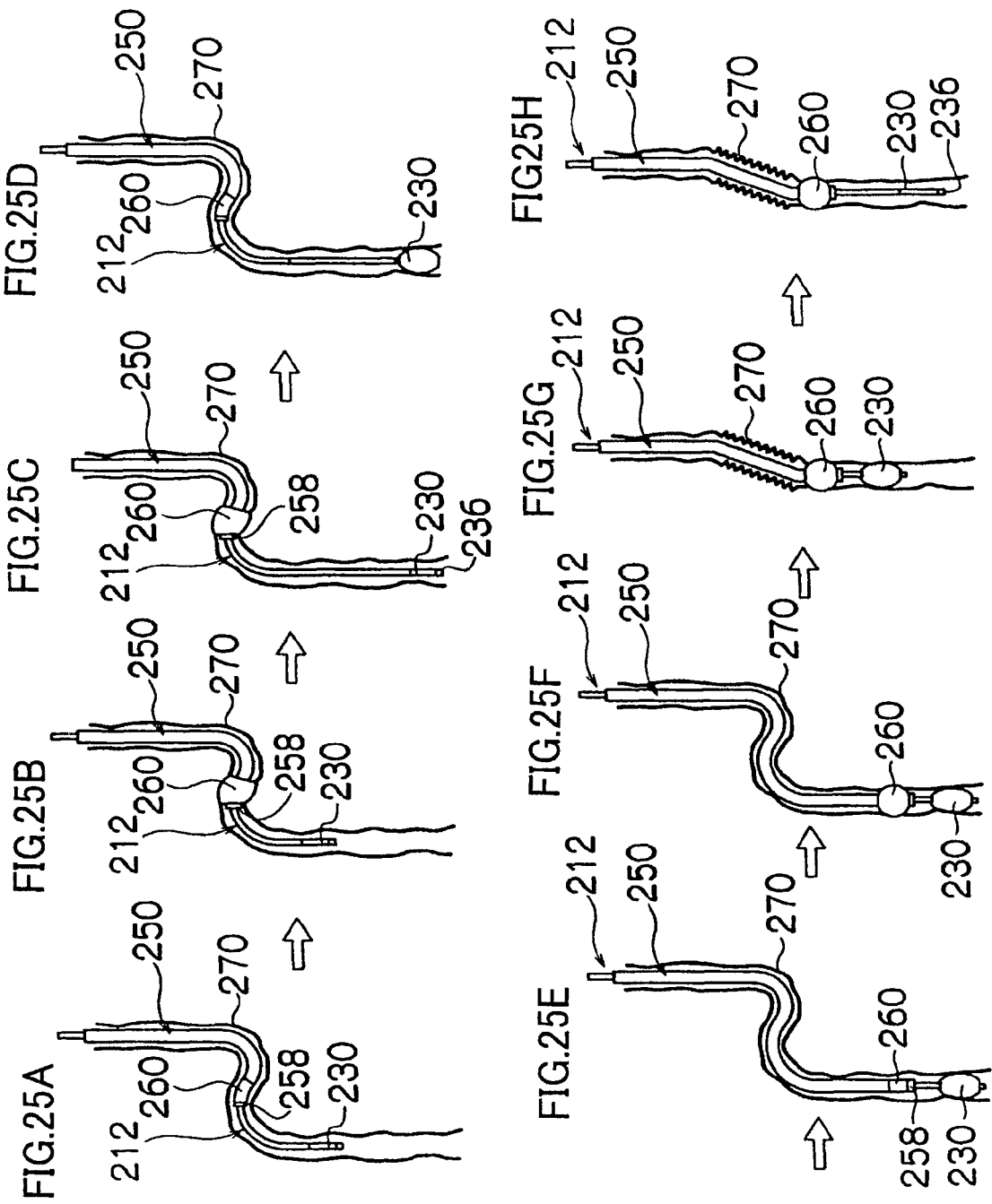

INSERTION ASSISTING TOOL FOR ENDOSCOPE

CROSS REFERENCE TO RELATED APPLICATIONS

This application is a continuation of and claims priority under 35 U.S.C. §§120/121 to U.S. patent application Ser. No. 11/892,615, filed on Aug. 24, 2007, now abandoned which is a Divisional of U.S. application Ser. No. 11/001,181, filed Dec. 2, 2004, now U.S. Pat. No. 8,088,063 which claims priority under 35 USC §119 to Japanese Application No. 2003-407979, filed Dec. 5, 2003; Japanese Application No. 2003-410641, filed Dec. 9, 2003; Application No. 2004-96451, filed Mar. 29, 2004; and Japanese Application No. 2004-322795, filed Nov. 5, 2004, the entire contents of each of which are incorporated herein by reference.

BACKGROUND OF THE INVENTION

1. Field of the Invention

The present invention relates to an insertion assisting tool for an endoscope, and particularly, relates to an insertion assisting tool of an endoscope which is used when an insertion section of the endoscope is inserted into a body cavity.

2. Description of the Related Art

When the insertion section of an endoscope is inserted into a deep alimentary canal such as a small intestine, by only pushing the insertion section into the deep alimentary canal, the force is difficult to transmit to a tip end of the insertion section due to complicated bending of an intestinal canal, and insertion into a deep part is difficult. Namely, if excessive bending and deflection occur to the insertion section, it is difficult to insert the insertion section further into a deeper part. Thus, there is proposed an endoscope apparatus which prevents excessive bending and deflection of the insertion section by inserting the insertion section into a body cavity with an insertion assisting tool called an over tube or a sliding tube attached to the insertion section of the endoscope, and inserting the insertion section into the body cavity while guiding the insertion section with this insertion assisting tool (for example, Japanese Patent Application Publication No. 10-248794).

Meanwhile, a double balloon type endoscope apparatus disclosed in Japanese Patent Application Publication No. 2002-301019 includes an endoscope with an inflatable and deflatable balloon attached to a tip end peripheral portion of an endoscope insertion section, and an over tube which serves as a guide at the time of insertion of the insertion section, with an inflatable and deflatable balloon attached to the tip end peripheral portion, and the endoscope insertion section inserted into the over tube. This double balloon type endoscope apparatus is for inserting the endoscope insertion section into a deep part of an alimentary canal by carrying out an insertion operation of the over tube and the endoscope insertion section and the inflation and deflation operations of the two balloons in accordance with a predetermined procedure.

SUMMARY OF THE INVENTION

However, the insertion assisting tool in Japanese Patent Application Publication No. 10-248794 has the problem that when the insertion assisting tool is inserted into a body cavity, a body fluid flows backward from a gap between the insertion assisting tool and the insertion section due to internal pressure of the body cavity, and leaks outside from a base end opening of the insertion assisting tool.

Similarly, the over tube of the double balloon type endoscope apparatus of Japanese Patent Application Publication No. 2002-301019 also has the problem that when the over tube is inserted into the body cavity, the body fluid flows backward from a gap between the over tube and the endoscope insertion section due to internal pressure of the body cavity (alimentary canal), and leaks outside from a base end opening of the over tube.

The present invention is made in view of the above circumstances, and has its object to provide an insertion assisting tool of an endoscope capable of preventing leakage of a fluid flowing backward from a body cavity.

In order to attain the above-described object, a first aspect of the present invention is, in an insertion assisting tool for an endoscope into which an insertion section of the endoscope is inserted from a base end portion side, comprising: a fluid sealing device which seals a space between a base end part of the insertion assisting tool and the endoscope insertion section, the space being formed while the insertion section of the endoscope is inserted into the base end portion side.

According to the first aspect, the liquid sealing device is provided, and therefore, a body fluid and a fluid such as a lubricating liquid, which is supplied to the insertion assisting tool, can be prevented from leaking from the space between the base end part of the insertion assisting tool and the endoscope insertion section.

In order to attain the aforesaid object, a second aspect of the present invention is, in an insertion assisting tool into which an insertion section of an endoscope is inserted, characterized by including a liquid storing part formed at a base end part side of the insertion assisting tool.

According to the second aspect, during an operation in which the insertion assisting tool is inserted into a body cavity, the body fluid, which flows backward from the gap between the insertion assisting tool and the insertion section due to internal pressure of the body cavity, is stored in the liquid storing part formed at the side of the base end part of the insertion assisting tool, and therefore, leakage of the body fluid flowing backward can be prevented.

According to a third aspect of the present invention, the insertion assisting section is characterized in that a suction device is attached to the liquid storing part of the insertion assisting tool. By attaching the suction device to the liquid storing part like this, the body fluid stored in the liquid storing part can be discharged from the liquid storing part, and therefore, leakage from the liquid storing part due to overflow can be prevented.

According to a fourth aspect of the present invention, the insertion assisting tool is characterized in that a liquid absorbing member is housed in the liquid storing part of the insertion assisting tool, and the liquid storing part is detachably attached to an insertion assisting tool body. The liquid absorbing member such as a sponge is housed in the liquid storing part, and thereby, the body fluid stored in the liquid storing part is held by the liquid absorbing member. Thereby, leakage of the body fluid from the liquid storing part can be prevented when the insertion assisting tool is used upside down due to the motion during operation. The liquid absorbing member which sufficiently absorbs the body fluid is removed by detaching the liquid storing part from the insertion assisting tool body, and is replaced with a new liquid absorbing member, thus making it possible to use the insertion assisting tool repeatedly.

According to a fifth aspect of the present invention, an inflatable and deflatable balloon is attached to an insertion section of the endoscope and/or a tip end part of the insertion assisting tool. The insertion assisting tool can be fixed to a body wall by inflating the balloon and closely fitting the balloon to the body wall such as an intestinal wall. In this state, the body wall is observed while performing a curving operation of the curving part of the endoscope insertion section, which protrudes from the tip end part of the insertion assisting tool, with the hand operation section. At this time, the insertion assisting tool is fixed to the body wall, and therefore, there is no fear that the curving part and the tip end part of the insertion section contact the insertion assisting tool, whereby curving operability of the curving part is enhanced. The insertion assisting tool having the balloon can be applied to a double-balloon type endoscope apparatus which uses the insertion assisting tool having the balloon by fitting the insertion assisting tool onto the endoscope insertion section also having a balloon. This endoscope apparatus makes it possible to observe an intestine by drawing in the intestine by carrying out the inflating and deflating operation of the two balloons, the insertion and extraction operation of the endoscope insertion section, and the insertion and extraction operation of the insertion assisting tool in accordance with a predetermined procedure.

In order to attain the above-described object, a sixth aspect of the present invention is characterized in that a cylindrical extendable and contractible member connecting respective base end parts of an insertion section of the endoscope and the insertion assisting tool in which the insertion section of the endoscope is inserted, said cylindrical extendable and contractible member covering the insertion section.

According to the sixth aspect of the invention, the respective base end parts of the insertion section of the endoscope and the insertion assisting tool into which the insertion section is inserted are connected by the cylindrical extendable and contractible member which covers the insertion section, and therefore, the body fluid flowing backward from the gap between the insertion assisting tool and the insertion section does not leak. Thereby, the leakage of the body fluid flowing backward from the body cavity can be prevented. Since the extendable and contractible member extends and contracts, the insertion operation and drawing-in operation of the insertion assisting tool and the insertion section can be performed smoothly.

According to a seventh aspect of the present invention, the insertion assisting tool is characterized in that the extendable and contractible member is an accordion-shaped member. Thereby, the extendable and contractible member can be easily constructed.

According to an eighth aspect of the present invention, the insertion assisting tool is characterized in that the extendable and contractible member is formed to have length by which a tip end part of the insertion assisting tool does not contact a first balloon of the insertion section when the extendable and contractible member is operated to extend most. As a result, at the stroke end when the insertion assisting tool is inserted deepest, the tip end part of the insertion assisting tool does not contact the first balloon, and therefore, the first balloon is not broken by contact of the tip end part of the insertion assisting tool. As for restraint at the time of the extension of the extendable and contractible member, the restraint can be achieved by setting the length and the number of the pleats of the accordion shape in the case of the accordion-shaped member having directivity in one direction in the extending and contracting direction. On the other hand, in the case of, for example, a bag-shaped member having no directivity in the extending and contracting direction, the restraint can be achieved by attaching restraining linear elements such as wires and strings, which restrain the extension amount, to the bag-shaped member.

According to a ninth aspect of the present invention, the insertion assisting tool is characterized in that a drain port is formed in the extendible member. The body fluid stored in the gap between the extendable and contractible member and the insertion section can be discharged to the outside from the gap via the drain port. A pump is separately connected to the drain port, and the liquid can be also discharged by the power of the power. Further, the body fluid stored in the gap may be discharged from the drain port by the pumping action occurring when the extendable and contractible member extends and contracts.

In order to achieve the above-described object, a tenth aspect of the present invention is, in the insertion assisting tool into which an insertion section of the endoscope is inserted, characterized by including a substantially cylindrical tube formed of an elastic body in which a smaller opening than a diameter of a base end part of the insertion assisting tool is formed at one end and a smaller opening than a diameter of the endoscope insertion section is formed at the other end, and characterized in that in the tube, the opening formed at the one end is attached to the base end part of the insertion assisting tool in close contact with the base end part, and the insertion section of the endoscope is slidably inserted through the tube with the insertion section of the endoscope closely fitted in the opening formed at the other end.

According to the tenth aspect, the opening formed at one end of the tube is attached to the base end part of the insertion assisting tool in close contact with the base end part by the elastic force, and the insertion section of the endoscope is slidably inserted through the opening in close contact with the opening formed at the other end of the tube by the elastic force. During the operation in which the insertion assisting tool is inserted into the body cavity, the body fluid flowing backward from the gap between the insertion assisting tool and the insertion section due to the internal pressure of the body cavity is stored in the tube without leaking from the tube. Namely, both ends of the tube are attached to the parts respectively in close contact with the parts by the elastic force, and therefore, the tube exhibits the function of the check valve. Thereby, the leakage of the body fluid can be prevented. In the case of the insertion assisting tool enhanced in slip property of the insertion section for the insertion assisting tool by supplying the lubricating liquid into the gap between the insertion assisting tool and the insertion section, it becomes possible to fill the lubricating liquid in the gap by allowing the tube to have the pot function of storing the lubricating liquid, and therefore, favorable slip property can be always obtained. Further, the supply amount and the number of supply times of the lubricating liquid can be reduced by the lubricating liquid pot function of the tube.

An eleventh aspect of the present invention is the invention which enhances the insertion and extraction operability of the insertion section with respect to the insertion assisting tool in the case where the tube is fitted to the aforesaid parts. The insertion section is inserted into the base end part of the insertion assisting tool with some degree of freedom. Namely, the space between the base end part of the insertion assisting tool and the insertion section is set to be comparatively larger than the spaces at the other positions, and the insertion and extraction operability of the operator is enhanced by making the insertion and extraction direction of the insertion section properly changeable by using the space. Accordingly, in the case where the tube is fitted, it is also necessary to keep this insertion and extraction operability.

Thus, according to the eleventh aspect, the insertion assisting tool is characterized in that the tube is formed in a size which satisfies a formula: $d>a-c+(b-a)/2$ where an inner diameter of the insertion assisting tool is a, a maximum diameter of the tube when the tube is attached to the insertion assisting tool is b, a diameter of an opening formed at the other end of the tube is c, and a distance from a fixed portion of the tube to the insertion assisting tool to an edge portion of the opening formed at the other end of the tube is d. As a result, when the insertion section is put aside as much as possible by using the space, the tube does not have tension, but has slack, and therefore, the insertion and extraction operability of the tube can be maintained.

According to the insertion assisting tool of the endoscope according to the present invention, the fluid sealing device which seals the space between the base end part of the insertion assisting tool and the insertion section of the endoscope, and prevents the fluid from leaking is provided, and therefore, the fluid can be prevented from leaking from the space between the base end part of the insertion assisting tool and the insertion section.

According to the insertion assisting tool of the endoscope according to the present invention, the body fluid flowing backward from the gap between the insertion assisting tool and the insertion section is stored in the liquid storing part formed at the base end part side of the insertion assisting tool, and therefore, leakage of the body fluid flowing backward can be prevented.

Further, according to the insertion assisting tool of the endoscope according to the present invention, the space between the insertion assisting tool and the insertion section is covered with the extendable and contractible member, and therefore, leakage of the body fluid flowing backward from the inside of the body cavity can be prevented. In addition, the extendable and contractible member extends and contracts, and therefore, the insertion operation and drawing-in operation of the insertion assisting tool and the insertion section can be smoothly performed.

According to the insertion assisting tool of the endoscope according to the present invention, the body fluid flowing backward from the space between the insertion assisting tool and the insertion section is stored in the tube having the function of the check valve, and therefore, the leakage of the body fluid flowing backward can be prevented.

BRIEF DESCRIPTION OF THE DRAWINGS

FIGS. 6A to 6H are explanatory views showing an operation method of the endoscope apparatus according to the present invention;

FIG. 7 is a partially enlarged sectional view showing another example of the over tube;

FIGS. 14A and 14B are explanatory views showing a stroke of an accordion-shaped extendable and contractible member of the over tube;

FIGS. 15A to 15H are explanatory views showing an operation method of the endoscope apparatus shown in FIG. 1;

FIGS. 16A and 16B are explanatory views showing an operation of a bag-shaped member of the over tube;

FIGS. 17A and 17B are sectional side views of the over tube provided with a drain port at the accordion-shaped extendable and contractible member of the over tube;

FIGS. 25A to 25H are explanatory views showing an operation method of the endoscope apparatus according to the present invention.

DETAILED DESCRIPTION OF THE PREFERRED EMBODIMENTS

Preferred embodiments of an insertion assisting tool of an endoscope according to the present invention will be explained in accordance with the following attached drawings.

Figure 1:
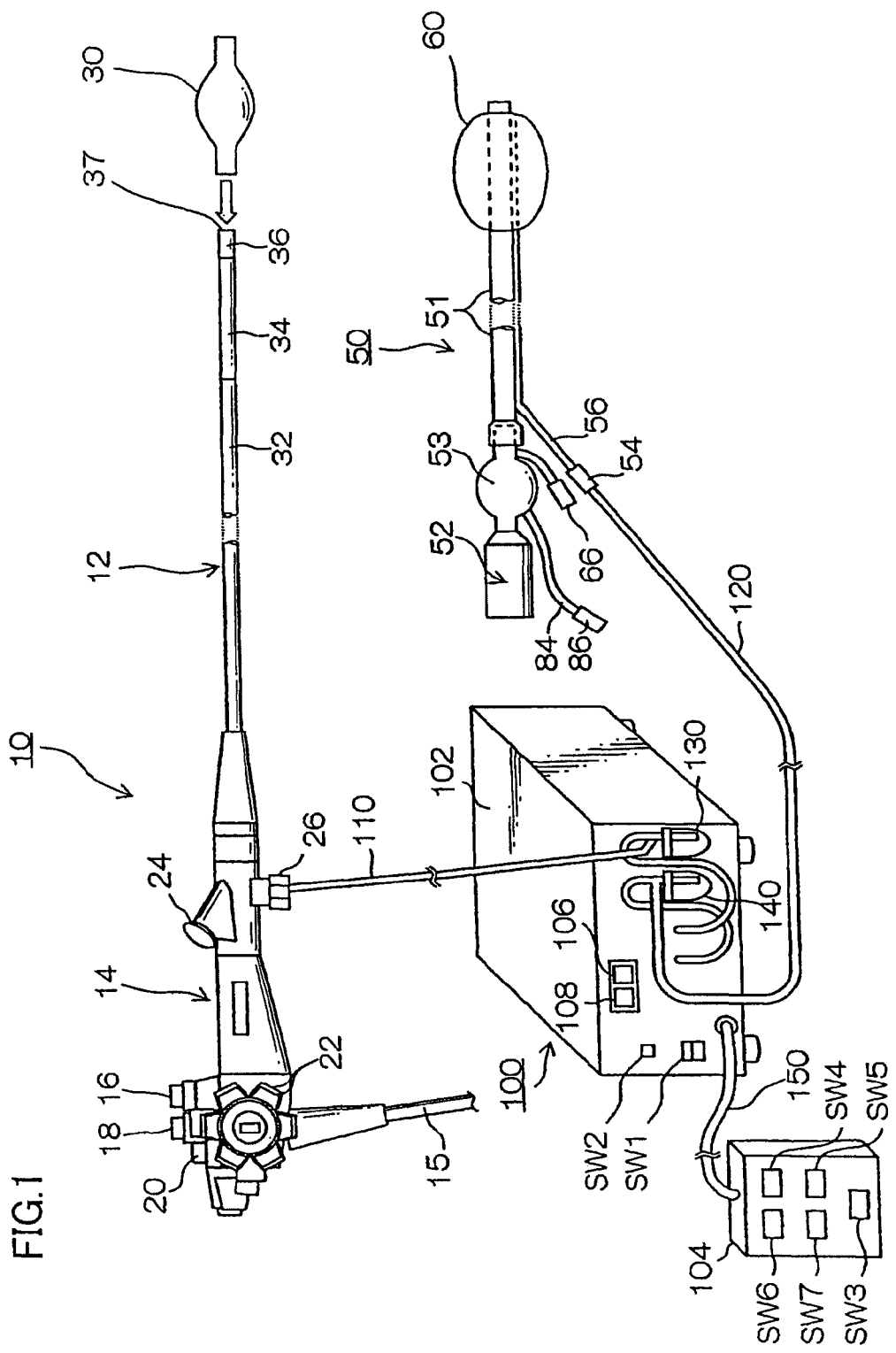
FIG. 1 is a system schematic diagram of an endoscope apparatus according to the present invention.

FIG. 1 shows a system schematic diagram of an endoscope apparatus to which an insertion assisting tool according to a first embodiment of the present invention is applied. The endoscope apparatus shown in the drawing is constructed by an endoscope 10, an over tube (corresponding to the insertion assisting tool) 50, and a balloon control device 100.

The endoscope 10 includes a hand operation section 14, and an insertion section 12 connected to the hand operation section 14. A universal cable 15 is connected to the hand operation section 14, and a connecter (not shown) connected to a processor and a light source device not shown is provided at a tip end of the universal cable 15.

On the hand operation section 14, an air/water passing button 16, a suction button 18, and a shutter button 20 which are operated by an operator are provided in parallel, and a pair of angle knobs 22 and 22, and a forceps insertion part 24 are respectively provided at predetermined positions. Further, the hand operation section 14 is provided with a balloon air port 26 for supplying air to a first balloon 30 and sucking air from the balloon 30.

The insertion section 12 is constructed by a flexible part 32, a curving part 34 and a tip end part 36. The curving part 34 is constructed by connecting a plurality of node rings to be able to curve, and is remotely operated to curve by the rotational operation of a pair of angle knobs 22 and 22 provided on the hand operation section 14. Thereby, a tip end surface 37 of the tip end part 36 can be directed in a desired direction.

Figure 2:
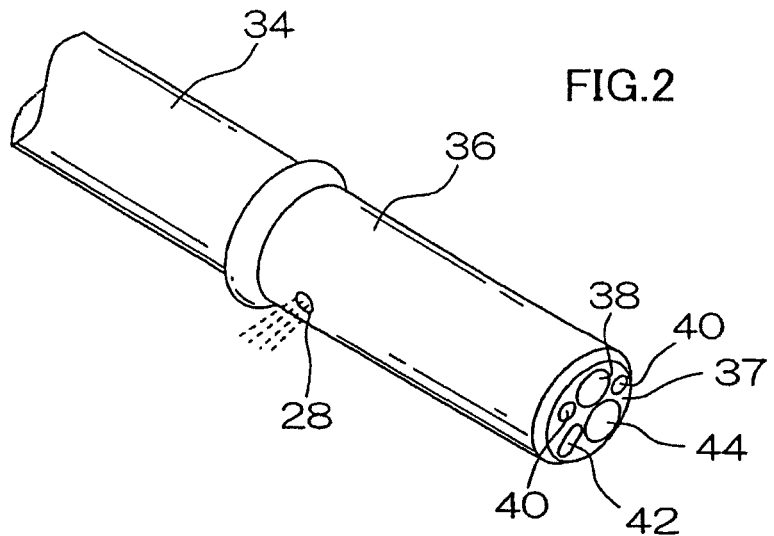
FIG. 2 is a perspective view showing a tip end part of an insertion section of an endoscope.

As shown in FIG. 2, the tip end surface 37 of the tip end part 36 is provided with an object optical system 38, an illumination lens 40, an air/water passing nozzle 42, a forceps port 44 and the like in predetermined positions. An air supply/suction port 28 is provided on an outer peripheral surface of the tip end part 36, and this air supply/suction port 28 communicates with the balloon air port 26 in FIG. 1 via an air supply tube (not shown) with an inner diameter of about 0.8 mm which is inserted into the insertion section 12. Accordingly, air is blown out of the air supply/suction port 28 of the tip end part 36 by supplying air to the balloon air port 26, and on the other hand, air is sucked from the air supply/suction port 28 by sucking air from the balloon air port 26.

Figure 3:
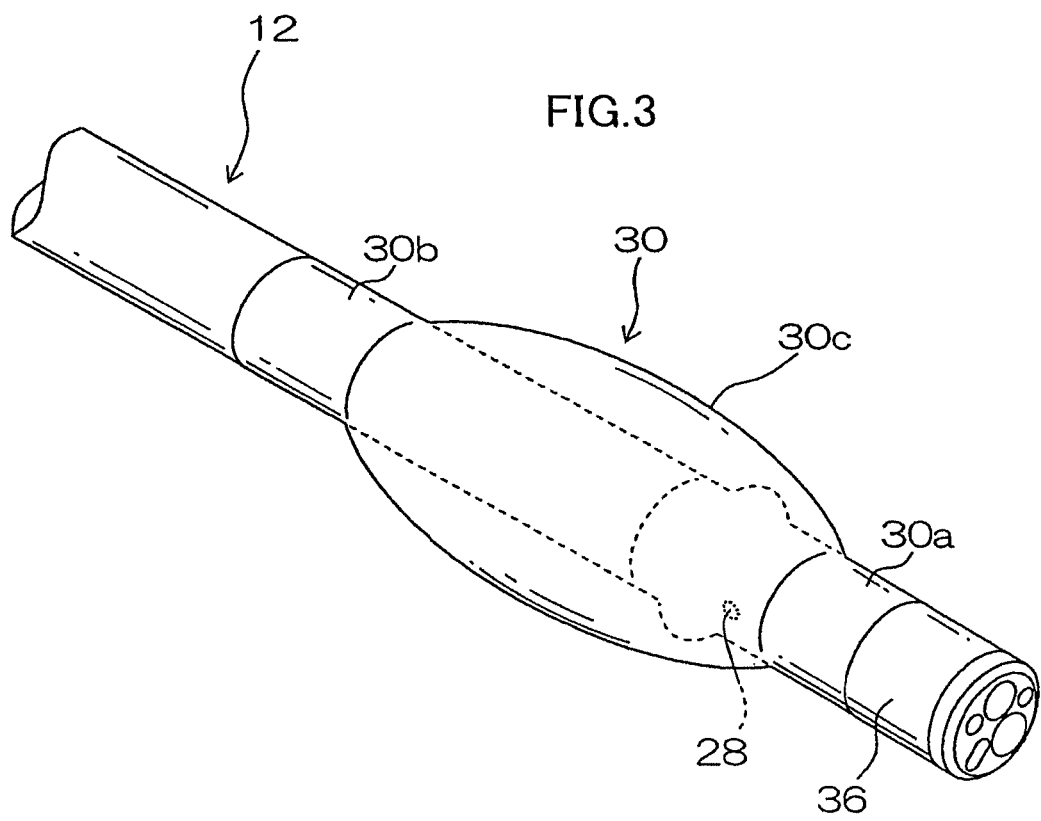
FIG. 3 is a perspective view showing the tip end part of the insertion section onto which a first balloon is fitted.

As shown in FIG. 1, the first balloon 30 constituted of an elastic body such as rubber is detachably attached to the tip end part 36 of the insertion section 12. The first balloon 30 is formed by a bulging portion 30c in a center and attaching portions 30a and 30b at both ends of the bulging portion 30c, and is attached to the tip end part 36 side so that the air supply/suction port 28 is located inside the bulging portion 30c as shown in FIG. 3. The attaching portions 30a and 30b are formed to have smaller diameters than the diameter of the tip end part 36, and after being closely fitted onto the tip end part 36 with their elastic forces, the attaching portions 30a and 30b are fixed with threads not shown wound around the attaching portions 30a and 30b. The fixation is not limited to the thread winding fixation, but the attaching portions 30a and 30b may be fixed to the tip end part 36 by fitting fixing rings onto the attaching portions 30a and 30b.

The first balloon 30 fitted onto the tip end part 36 has its bulging portion 30c inflated in a substantially spherical shape by blowing air from the air supply/suction port 28 shown in FIG. 2. On the other hand, by sucking air from the air supply/suction port 28, the bulging portion 30c is deflated and is closely fitted onto the outer peripheral surface of the tip end part 36.

Figure 4:
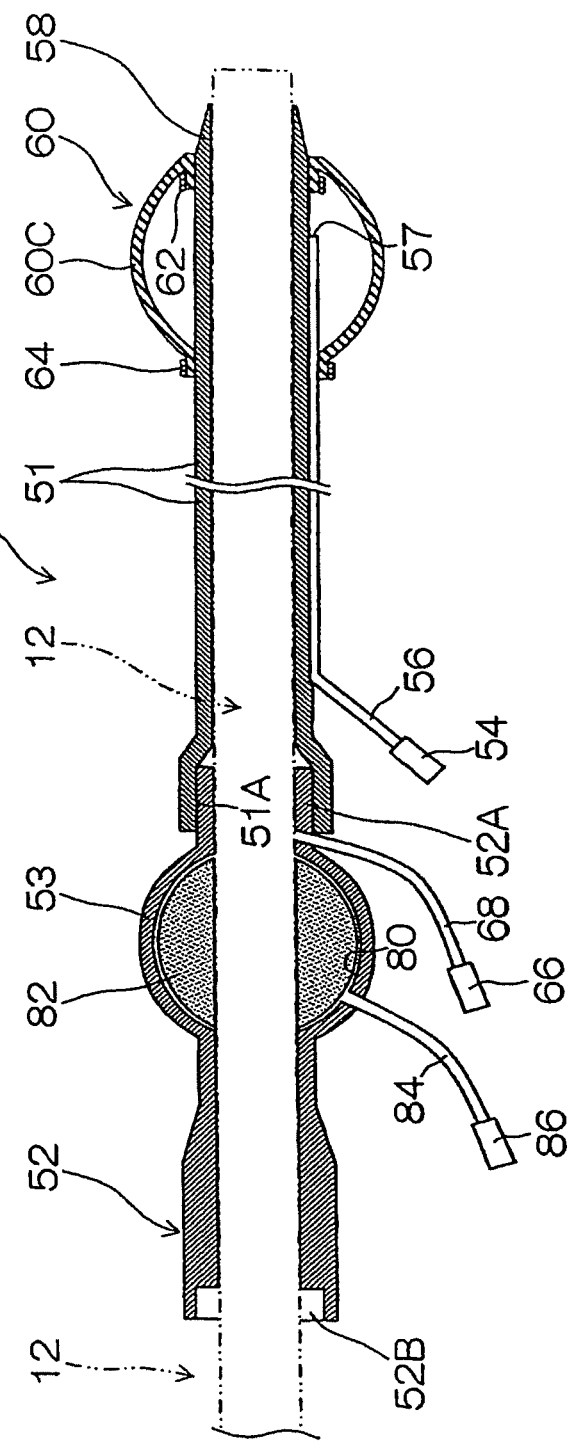
FIG. 4 is a sectional side view showing an over tube.
Figure 5:
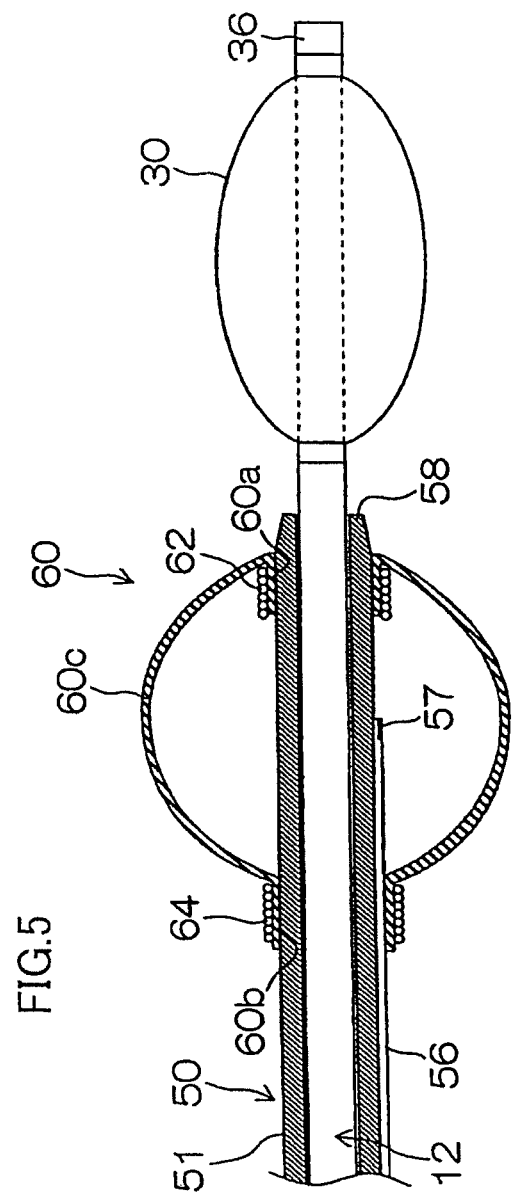
FIG. 5 is a sectional side view showing a tip end portion of the over tube through which the insertion section is inserted.

The over tube 50 shown in FIG. 1 is formed by a tube body 51, and a gripping part 52 in which a liquid storing part 53 is formed. The tube body 51 is formed into a cylindrical shape and has a slightly larger inner diameter than an outer diameter of the insertion section 12, as shown in FIGS. 4 and 5. The tube body 51 is constructed by covering an outer side of a flexible resin tube made of urethane or the like with lubricating coat and covering an inner side with the lubricating coat. A connecting port 52A formed at a tip end of the rigid gripping part 52 is fitted onto a base end opening 51A of the tube body 51 in a watertight state, and the gripping part 52 is constructed to be attachable and detachable with respect to the tube body 51. The insertion section 12 is inserted toward the tube body 51 from the base end opening 52B of the gripping part 52.

As shown in FIG. 4, a balloon air port 54 is provided at the base end side of the tube body 51. An air supply tube 56 with an inner diameter of about 1 mm is connected to the balloon air port 54, and this tube 56 is bonded to an outer peripheral surface of the tube body 51 and is provided to extend to a tip end portion of the tube body 51.

A tip end 58 of the tube body 51 is formed into a tapered shape. A second balloon 60 constituted of an elastic body such as rubber is fitted onto the base end side of the tip end 58 of the tube body 51. The second balloon 60 is fitted in the state in which the tube body 51 penetrates through the balloon 60, and is constructed by a bulging portion 60c in a center, and attaching portions 60a and 60b at both ends of the bulging portion 60c. The attaching portion 60a at the tip end side is folded back to the inside of the bulging portion 60c, and the attaching portion 60a folded back is fixed to the tube body 51 with an X-ray contrast thread 62 wound around the attaching portion 60a which is folded back. The attaching portion 60b at the base end side is disposed outside the second balloon 60, and is fixed to the tube body 51 with a thread 64 wound around the attaching portion 60b.

The bulging portion 60c is formed into a substantially spherical shape in a natural state (the state in which the bulging portion 60c does not inflate or deflate), and as for the size, the bulging portion 60c is formed to be larger than the size of the first balloon 30 in a natural state (the state in which the balloon 30 does not inflate or deflate). Accordingly, when the air is supplied to the first balloon 30 and the second balloon 60 at the same pressure, the outer diameter of the bulging portion 60c of the second balloon becomes larger than the outer diameter of the bulging portion 30c of the first balloon 30. The outer diameter of the second balloon 60 is constructed so as to be φ50 mm when the outer diameter of the first balloon 30 is φ25 mm, for example.

The aforementioned tube 56 is opened in the inside of the bulging portion 60c, and an air supply/suction port 57 is formed. Accordingly, when air is supplied from the balloon air port 54, the air is blown from the air supply/suction port 57 and thereby, the bulging portion 60c is inflated. When air is sucked from the balloon air port 54, the air is sucked from the air supply/suction portion 57, and the second balloon 60 is deflated. Reference numeral 66 in FIG. 4 designates an inlet port for filling a lubricant such as water into the tube body 51, and the inlet port 66 communicates with the vicinity of a connecting port 52A formed at a tip end of the gripping part 52 via a tube 68 with a thin diameter.

The liquid storing part 53 of the gripping part 52 is formed into a spherical shape having a larger diameter than the diameter of the tube body 51, and an arc-shaped recessed portion 80 is formed inside the liquid storing part 53. A sponge (liquid absorbing member) 82 formed into a donut shape is hosed in this recessed portion 80. The inner diameter of the sponge 82 is formed to be larger than the outer diameter of the insertion section 12, and therefore, it causes no problem in insertion of the insertion section 12. On the other hand, when liquid leakage is prevented by an O-ring or the like, the O-ring has to be fastened to the insertion section 12, which causes the problem of impairing insertion easiness, and the present example can solve such a problem. The shape of the sponge is not limited to the donut shape, but the sponge may be formed into a substantially cylindrical shape. By forming a split in the sponge formed into the donut shape or substantially cylindrical shape, the insertion section 12 can be removed from the sponge via the split in the state in which the insertion section 12 is inserted through the sponge.

At the time of an operation, the body fluid which flows backward from a gap between the tube body 51 and the insertion section 12 stays in the recessed portion 80 and absorbed in the sponge 82, thus preventing the liquid leakage from the recessed portion 80. A water intake port 86 communicates with the recessed portion 80 of the liquid storing part 53 via a thin-diameter tube 84, and by connecting a suction device such as an injector and a pump to this water intake port 86, and making the suction device perform a suction operation, the liquid stored in the recessed portion 80, and the liquid absorbed in the sponge 82 is sucked and removed from the liquid storing part 53.

Meanwhile, the balloon control device 100 in FIG. 1 is the device which supplies and sucks fluid such as air to and from the first balloon 30, and supplies and sucks fluid such as air to and from the second balloon 60. The balloon control device 100 is constructed by a device body 102 including a pump, a sequencer and the like not shown, and a hand switch 104 for remote control.

A front panel of the device body 102 is provided with a power supply switch SW1, a stop switch SW2, a pressure gauge 106 for the first balloon 30 and a pressure gauge 108 for the second balloon 60. A tube 110 for supplying/sucking air to and from the first balloon 30, and a tube 120 for supplying/sucking air to and from the second balloon 60 are attached to the front panel of the device body 102. Liquid storing tanks 130 and 140 for storing body fluid, which flows backward from the first balloon 30 and the second balloon 60 when the first balloon 30 and the second balloon 60 are broken, are respectively provided at midpoints of the respective tubes 110 and 120.

Meanwhile, the hand switch 104 is provided with a similar stop switch SW3 to the stop switch SW2 at the side of the device body 102, an ON/OFF switch SW4 for supporting pressurization/decompression of the first balloon 30, a pose switch SW5 for keeping the pressure of the first balloon 30, an ON/OFF switch SW6 for supporting pressurization/decompression of the second balloon 60, and a pose switch SW7 for keeping the pressure of the second balloon 60. This hand switch 104 is electrically connected to the device body 102 via a cable 150.

The balloon control device 100 thus constructed supplies air to the first balloon 30 and the second balloon 60 and inflates the first balloon 30 and the second balloon 60, and controls the air pressure at a fixed value to keep the first balloon 30 and the second balloon 60 in the inflated state. The balloon control device 100 sucks air from the first balloon 30 and the second balloon 60 and deflates the first balloon 30 and the second balloon 60, and controls the air pressure at a fixed value to keep the first balloon 30 and the second balloon 60 in the deflated state.

Next, an operation method of the endoscope apparatus will be explained in accordance with FIGS. 6A to 6H.

First, as shown in FIG. 6A, the insertion section 12 is inserted into an intestinal canal (for example, descending limb of duodenum) 70 in the state in which the over tube 50 covers the insertion section 12. At this time, the first balloon 30 and the second balloon 60 are deflated.

Next, as shown in FIG. 6B, in the state in which the tip end 58 of the over tube 50 is inserted into a bent portion of the intestinal canal 70, air is supplied to the second balloon 60 to inflate the second balloon 60. As a result, the second balloon 60 is caught by the intestinal canal 70, and the tip end 58 of the over tube 50 is fixed to the intestinal canal 70.

Next, as shown in FIG. 6C, only the insertion section 12 of the endoscope 10 is inserted to a deep part of the intestinal canal 70. Then, as shown in FIG. 6D, air is supplied to the first balloon 30 to inflate the first balloon 30. As a result, the first balloon 30 is fixed to the intestinal canal 70. In this case, the first balloon 30 is smaller in the size at the time of inflation than the second balloon 60, and therefore the burden exerted on the intestinal canal 70 is small, thus making it possible to prevent damage to the intestinal canal 70.

Next, after air is sucked from the second balloon 60 to deflate the second balloon 60, the over tube 50 is pushed in, and inserted along the insertion section 12, as shown in FIG. 6E. Then, after the tip end 58 of the over tube 50 is pushed into the vicinity of the first balloon 30, air is supplied to the second balloon 60 to inflate the second balloon 60 as shown in FIG. 6F. As a result, the second balloon 60 is fixed to the intestinal canal 70. Namely, the intestinal canal 70 is gripped by the second balloon 60.

Next, as shown in FIG. 6G, the over tube 50 is drawn in. Thereby, the intestinal canal 70 contracts substantially straight, and excessive deflection and bending of the over tube 50 are eliminated. When the over tube 50 is drawn in, both the first balloon 30 and the second balloon 60 are caught in the intestinal canal 70, but the friction resistance of the first balloon 30 is smaller than the friction resistance of the second balloon 60. Therefore, even if the first balloon 30 and the second balloon 60 move to relatively separate, the first balloon 30 with small friction resistance slides with respect to the intestinal canal 70, and therefore, it does not happen that the intestinal canal 70 is damaged by being pulled by both the balloons 30 and 60.

Next, as shown in FIG. 6H, air is sucked from the first balloon 30 to deflate the first balloon 30. Then, the tip end part 36 of the insertion section 12 is inserted into as deep a part of the intestinal canal 70 as possible. Namely, the insertion operation as shown in FIG. 6C is performed again. Thereby, the tip end part 36 of the insertion section 12 can be inserted into a deep part of the intestinal canal 70. When the insertion section 12 is further inserted into a deep part, the pushing operation as shown in FIG. 6E is performed after the fixing operation as shown in FIG. 6D is performed, the gripping operation as shown in FIG. 6F and the drawing-in operation as shown in FIG. 6G, and the inserting operation as shown in FIG. 6H are repeatedly performed in sequence. Thus, the insertion section 12 can be further inserted into a deep part of the intestinal canal 70.

During such an operation, the body fluid which flows backward from the gap between the tube body 51 of the over tube 50 and the insertion section 12 (see FIG. 4) due to the internal pressure of the intestinal canal 70 stays in the recessed portion 80 of the liquid storing part 53 formed in the gripping part 52, and therefore, the body fluid flowing backward can be prevented from leaking from the base end opening 52B of the gripping part 52.

The body fluid stored in the liquid storing part 53 can be discharged from the liquid storing part 53 by sucking the body fluid stored in the liquid storing part 53 by the suction device such as an injector connected to the suction port 86, and therefore, leakage of the body fluid from the liquid storing part 53 due to overflow can be prevented.

Further, the sponge 82 is housed in the liquid storing part 53, and therefore, the body fluid stored in the liquid storing part 53 can be held by the sponge 82. Therefore, leakage of the body fluid from the liquid storing part 53 when the over tube 50 is used upside down in the motion during operation can be prevented. The sponge 82 which sufficiently absorbs the body fluid is taken out of the liquid storing part 53 after the gripping part 52 is detached from the tube body 51, and exchanged with a new sponge 82. Thus, the repeated use of the gripping part 52 is possible.

In the embodiment, the example of the over tube 50 having the balloon is explained, but the present invention can be also applied to a sliding tube which guides the endoscope insertion section into a body cavity without a balloon. The structure of the gripping part 52 is not limited to the example in FIG. 4, but as shown in FIG. 7, an opening 88 for opening the liquid storing part 53 is formed in order to make it easy to remove the sponge 82 from the recessed portion 80, and a donut-shaped cap 90 may be detachably fitted to the opening 88. According to this structure, the sponge 82 can be easily removed from the recessed portion 80 by only taking the cap 90 from the opening 88.

Figure 8:
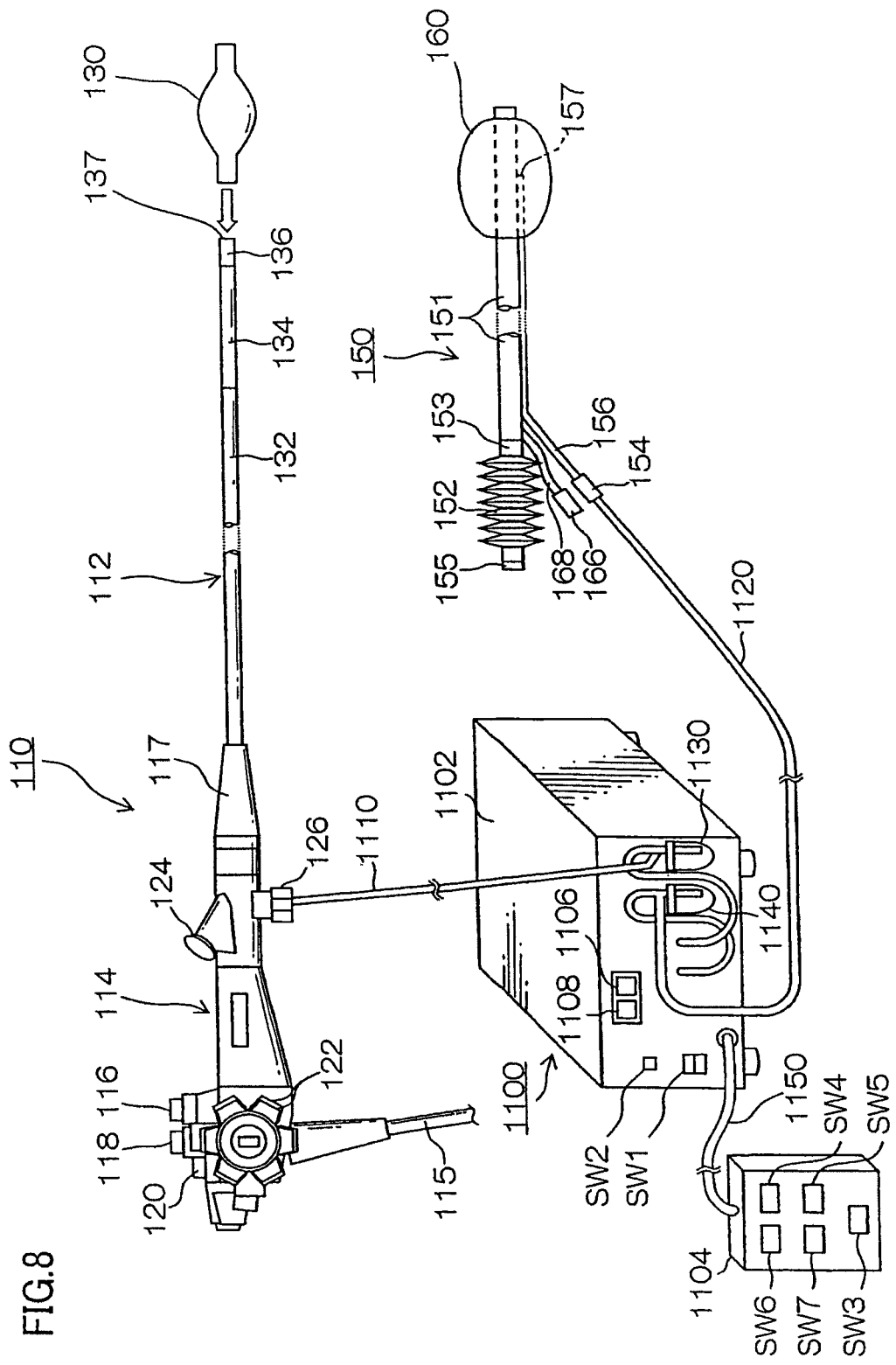
FIG. 8 is a system schematic diagram of an endoscope apparatus to which the over tube according to the present invention is applied.

FIG. 8 shows a system schematic diagram of an endoscope apparatus to which an over tube according to a second embodiment of the present invention is applied. The endoscope apparatus shown in the drawing is constructed by an endoscope 110, an over tube 150, and a balloon control device 1100.

The endoscope 110 includes a hand operation section 114, and an insertion section 112 connected to the hand operation section 114. A universal cable 115 is connected to the hand operation section 114, and a connecter (not shown) connected to a processor and a light source device not shown is provided at a tip end of the universal cable 115.

On the hand operation section 114, an air/water passing button 116, a suction button 118, and a shutter button 120 which are operated by an operator are provided in parallel, and a pair of angle knobs 122 and 122 and a forceps insertion section 124 are respectively provided in predetermined positions. Further, the hand operation section 114 is provided with a balloon air port 126 for supplying air to a first balloon 130 and sucking air from the first balloon 130.

The insertion section 112 is constructed by a flexible part 132, a curving part 134 and a tip end rigid part 136. The curving part 134 is constructed by connecting a plurality of node rings to be able to curve, and is remotely operated to curve by the rotational operation of a pair of angle knobs 122 and 122 provided on the hand operation section 114. Thereby, a tip end surface 137 of the tip end part 136 can be directed in a desired direction.

Figure 9:
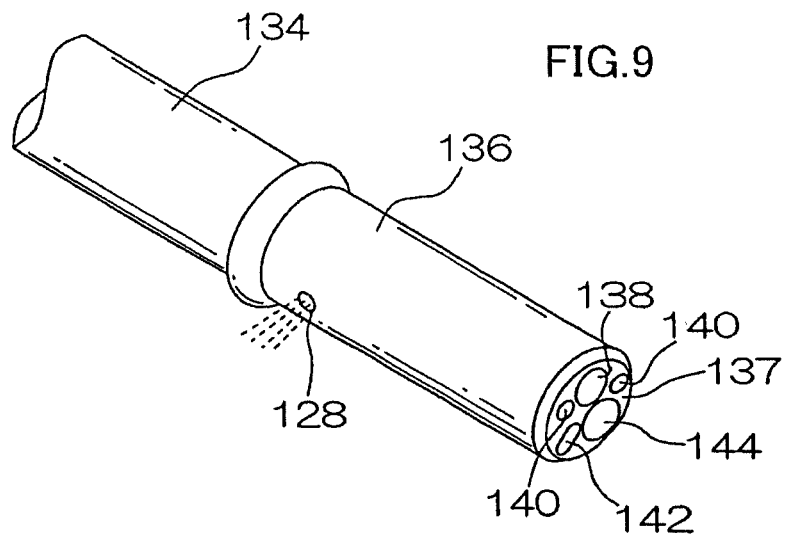
FIG. 9 is a perspective view showing a tip end part of an insertion section of the endoscope.

As shown in FIG. 9, the tip end surface 137 of the tip end part 136 is provided with an object optical system 138, an illumination lens 140, an air/water passing nozzle 142, a forceps port 144 and the like in predetermined positions. An air supply/suction port 128 is provided on an outer peripheral surface of the tip end part 136, and this air supply/suction port 128 communicates with the balloon air port 126 in FIG. 8 via an air supply tube (not shown) with an inner diameter of about 0.8 mm which is inserted into the insertion section 112. Accordingly, air is blown out of the air supply/suction port 128 of the tip end part 136 by supplying air to the balloon air port 126, and on the other hand, air is sucked from the air supply/suction port 128 by sucking air from the balloon air port 126.

Figure 10:
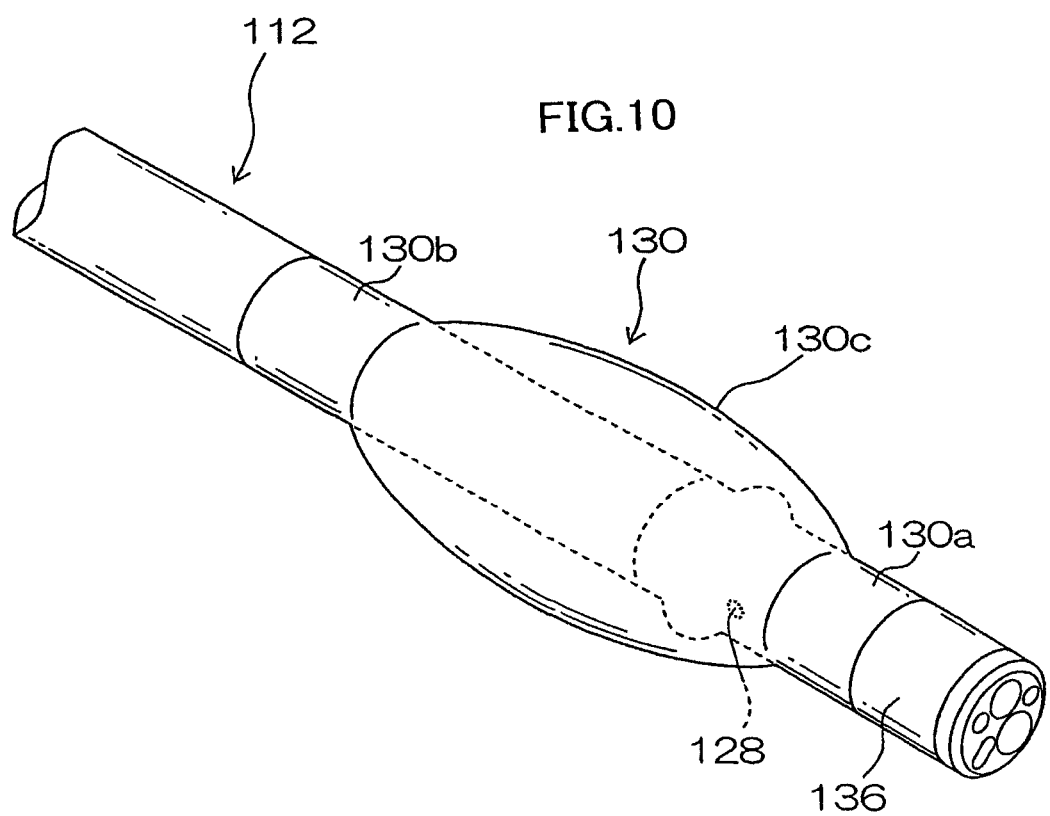
FIG. 10 is a perspective view showing a tip end rigid part of the insertion section onto which the first balloon is fitted.

As shown in FIG. 8, a first balloon 130 constituted of an elastic body such as rubber is detachably attached to the tip end part 136 of the insertion section 112. The first balloon 130 is formed by a bulging portion 130*c* in a center and attaching portions 130*a* and 130*b* at both ends of the bulging portion 130*c*, and is attached to the tip end part 136 side so that the air supply/suction port 128 is located inside the bulging portion 130*c* as shown in FIG. 10. The attaching portions 130*a* and 130*b* are formed to have smaller diameters than the diameter of the tip end portion 136, and after being closely fitted onto the tip end part 136 with their elastic forces, the attaching portions 130*a* and 130*b* are fixed with threads not shown wound around the attaching portions 130*a* and 130*b*. The fixation is not limited to the thread winding fixation, but the attaching portions 130*a* and 130*b* may be fixed to the tip end part 136 by fitting fixing rings onto the attaching portions 130*a* and 130*b*.

The first balloon 130 fitted onto the tip end part 136 has its bulging portion 130*c* inflated into a substantially spherical shape by blowing air from the air supply/suction port 128 shown in FIG. 9. On the other hand, by sucking air from the air supply/suction port 128, the bulging portion 130*c* is deflated and is closely fitted onto the outer peripheral surface of the tip end part 136.

The over tube 150 shown in FIG. 8 is formed by a tube body 151, and an accordion-shaped extendable and contractible member 152. The tube body 151 is formed into a cylindrical shape and has a slightly larger inner diameter than an outer diameter of the insertion section 112, as shown in FIGS. 4 and 5. The tube body 151 is constructed by coveting an outer side of a flexible resin tube made of urethane or the like with lubricating coat and covering an inner side with the lubricating coat.

Figure 13:
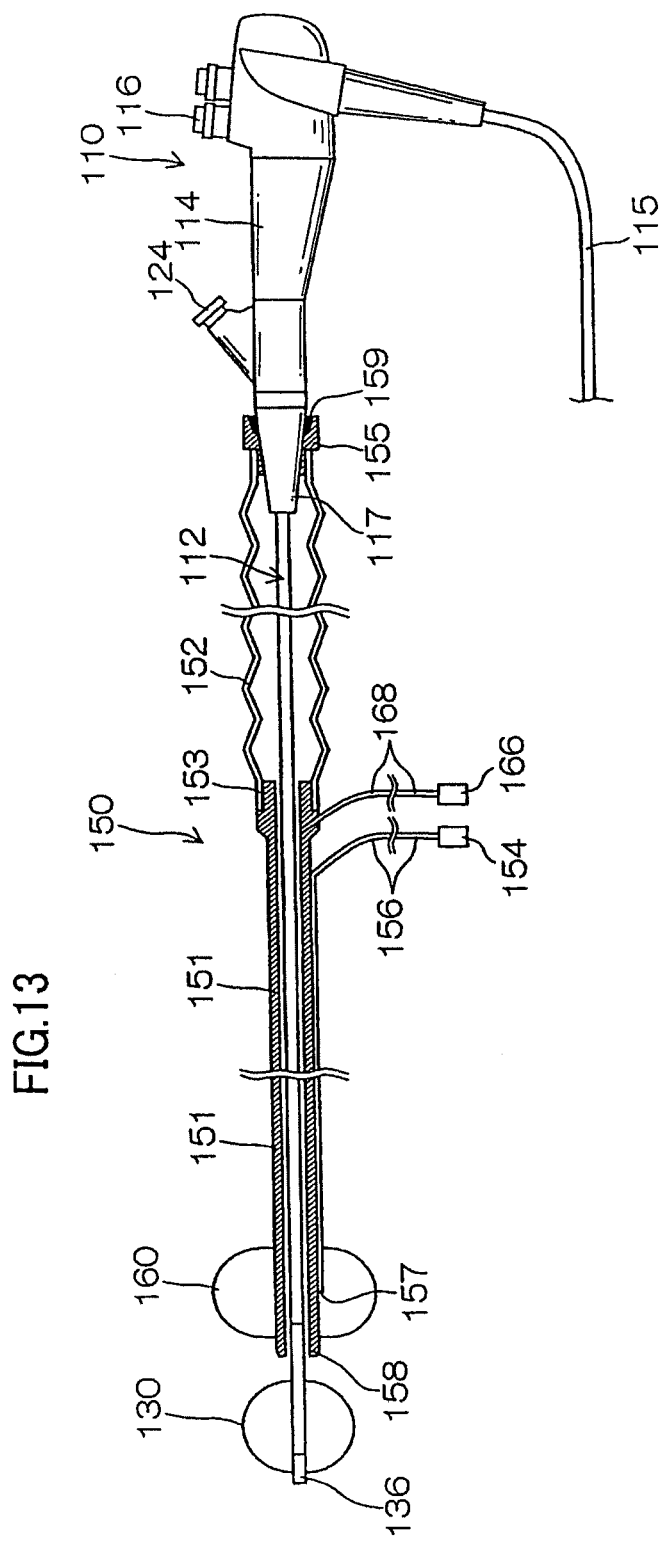
FIG. 13 is a sectional side view of the over tube which is fitted onto the endoscope insertion section.

The accordion-shaped extendable and contractible member 152 is made of a flexible resin material constituted of urethane or the like, and a ring-shaped fitting member 153, which is fixed to a tip end of the accordion-shaped extendable and contractible member 152, is fitted (connected) onto a base end opening 151A of the tube body 151 in the watertight state. A ring-shaped fitting member 155 fixed to a base end portion of the accordion-shaped extendable and contractible member 152 is fitted onto (connected to) a fold preventing part (base part of the insertion section) 117 in a substantially circular conical shape, which is formed at the tip end of the hand operating section 114, in the watertight state via a packing 159 as shown in FIG. 13. Thereby, the respective base end portions of the over tube 150 and the insertion section 112 are connected by the accordion-shaped extendable and contractible member 152. By using taper surface of the fold preventing part 117, fitting of the ring-shaped fitting member 155 can be easily performed in the water tight state.

Figure 11:
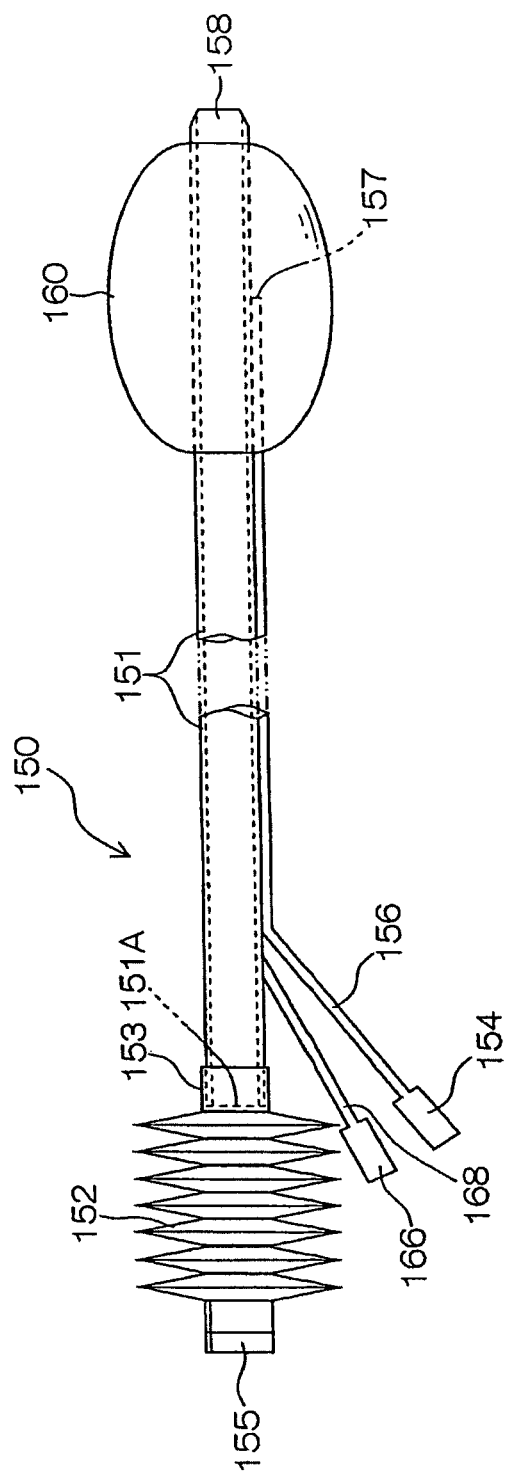
FIG. 11 is a side view of the over tube.
Figure 12:
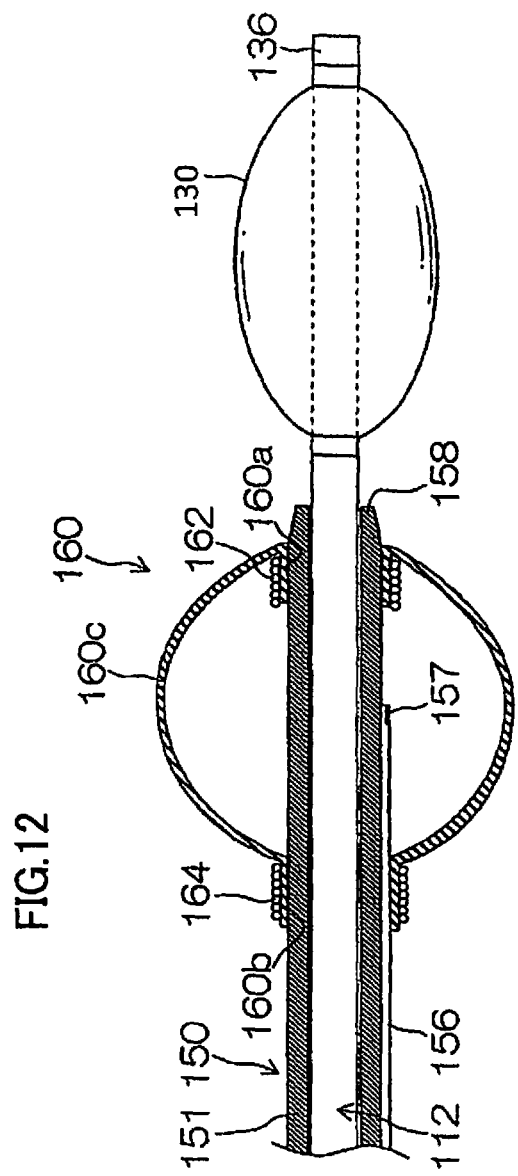
FIG. 12 is a sectional side view showing the tip end part of the over tube through which the insertion section is inserted.

As shown in FIG. 8, a balloon air port 154 is provided at the base end side of the tube body 151. An air supply tube 156 with an inner diameter of about 1 mm is connected to the balloon air port 154, and this tube 156 is bonded to an outer peripheral surface of the tube body 151 and is provided to extend to a tip end portion of the tube body 151, as shown in FIGS. 11 and 12.

A tip end 158 of the tube body 151 is formed into a tapered shape. A second balloon 160 constituted of an elastic body such as rubber is fitted onto the base end side of the tip end 158 of the tube body 151. The second balloon 160 is fitted in the state in which the tube body 151 penetrates through the balloon 160 as shown in FIG. 12, and is constructed by a bulging portion 160*c*, and attaching portions 160*a* and 160*b* at both ends of the bulging portion 160*c*. The attaching portion 160*a* at the tip end side is folded back to the inside of the bulging portion 160*c*, and the attaching portion 160*a* that is folded back is fixed to the tube body 151 with an X-ray contrast thread 162 wound around the attaching portion 160*a* that is folded back. The attaching portion 160*b* at the base end side is disposed outside the second balloon 160, and is fixed to the tube body 151 with a thread 164 wound around the attaching portion 160*b*.

The bulging portion 160*c* is formed into a substantially spherical shape in a natural state (the state in which the bulging portion 160*c* does not inflate or deflate), and as for the size, the bulging portion 160*c* is formed to be larger than the size of the first balloon 130 in a natural state (the state in which the balloon 130 does not inflate or deflate). Accordingly, when the air is supplied to the first balloon 130 and the second balloon 160 at the same pressure, the outer diameter of the bulging portion 160c of the second balloon 160 becomes larger than the outer diameter of the bulging portion 130c of the first balloon 130. The outer diameter of the second balloon 160 is constructed so as to be φ50 mm when the outer diameter of the first balloon 130 is φ25 mm, for example.

The aforementioned tube 156 is opened in the inside of the bulging portion 160c, and an air supply/suction port 157 is formed. Accordingly, when air is supplied from the balloon air port 154, the air is blown from the air supply/suction port 157 and thereby, the bulging portion 160c is inflated. When air is sucked from the balloon air port 154, the air is sucked from the air supply/suction port 157, and the second balloon 160 is deflated.

Reference numeral 166 in FIG. 11 designates an inlet port for filling a lubricating liquid such as water into the tube body 151, and the inlet port 166 communicates with the base end portion side of the tube body 151 via a tube 168 with a thin diameter.

Incidentally, the accordion-shaped extendable and contractible member 152 is repeatedly extended and contracted between the most extended state shown in FIG. 14A and the most contracted state shown in FIG. 14B during operation of the endoscope. Here, in setting the length of the accordion-shaped extendable and contractible member 152, the length is set so that a difference A between the most extended time and the most contracted time of the accordion-shaped extendable and contractible member 152 satisfies a moving amount B necessary for the operation of the endoscope (for example, 40 cm<A<60 cm), and keeps a space C by which the tip end 158 of the over tube 150 dose not abut to the first balloon 130 at the most extended time. The length of the accordion-shaped extendable and contractible member 152 is adjusted by the length of the pleat and the number of pleats of the accordion-shaped member.

Meanwhile, the balloon control device 1100 in FIG. 8 is the device which supplies and sucks fluid such as air to and from the first balloon 130, and supplies and sucks fluid such as air to and from the second balloon 160. The balloon control device 1100 is constructed by a device body 1102 including a pump, a sequencer and the like not shown, and a hand switch 1104 for remote control.

A front panel of the device body 1102 is provided with a power supply switch SW1, a stop switch SW2, a pressure gauge 1106 for the first balloon 130 and a pressure gauge 1108 for the second balloon 160. A tube 1110 for supplying/sucking air to and from the first balloon 130, and a tube 1120 for supplying/sucking air to and from the second balloon 160 are attached to the front panel of the device body 1102. Liquid storing tanks 1130 and 1140 for storing body fluid, which flows backward from the first balloon 130 and the second balloon 160 when the first balloon 130 and the second balloon 160 are broken, are respectively provided at midpoints of the respective tubes 1110 and 1120.

Meanwhile, the hand switch 1104 is provided with a similar stop switch SW3 to the stop switch SW2 at the side of the device body 1102, an ON/OFF switch SW4 for supporting pressurization/decompression of the first balloon 130, a pose switch SW5 for keeping the pressure of the first balloon 130, an ON/OFF switch SW6 for supporting pressurization/decompression of the second balloon 160, and a pose switch SW7 for keeping the pressure of the second balloon 160. This hand switch 1104 is electrically connected to the device body 1102 via a cable 1150.

The balloon control device 1100 which is constructed as above supplies air to the first balloon 130 and the second balloon 160 and inflates the first balloon 130 and the second balloon 160, and controls the air pressure at a fixed value to keep the first balloon 130 and the second balloon 160 in the inflated state. The balloon control device 1100 sucks air from the first balloon 130 and the second balloon 160 and deflates the first balloon 130 and the second balloon 160, and controls the air pressure at a fixed value to keep the first balloon 130 and the second balloon 160 in the deflated state.

Next, an operation method of the endoscope apparatus will be explained in accordance with FIGS. 15A to 15H.

First, as shown in FIG. 15A, the insertion section 112 is inserted into an intestinal canal (for example, descending limb of duodenum) 170 in the state in which the over tube 150 covers the insertion section 112. At this time, the first balloon 130 and the second balloon 160 are deflated.

Next, as shown in FIG. 15B, in the state in which the tip end 158 of the over tube 150 is inserted up to a bent portion of the intestinal canal 170, air is supplied to the second balloon 160 to inflate the second balloon 160. As a result, the second balloon 160 is caught by the intestinal canal 170, and the tip end 158 of the over tube 150 is fixed to the intestinal canal 170.

Next, as shown in FIG. 15C, only the insertion section 112 of the endoscope 110 is inserted into a deep part of the intestinal canal 170. Then, as shown in FIG. 15D, air is supplied to the first balloon 130 to inflate the first balloon 130. As a result, the first balloon 130 is fixed to the intestinal canal 170. In this case, the first balloon 130 is smaller in size at the time of inflation than the second balloon 160, and therefore, the burden exerted on the intestinal canal 170 is small, thus making it possible to prevent damage to the intestinal canal 170.

Next, after air is sucked from the second balloon 160 to deflate the second balloon 160, the over tube 150 is pushed in, and inserted along the insertion section 112, as shown in FIG. 15E. Then, after the tip end 158 of the over tube 150 is pushed into the vicinity of the first balloon 130, air is supplied to the second balloon 160 to inflate the second balloon 160 as shown in FIG. 15F. As a result, the second balloon 160 is fixed to the intestinal canal 170. Namely, the intestinal canal 170 is gripped by the second balloon 160.

Next, as shown in FIG. 15G, the over tube 150 is drawn in. Thereby, the intestinal canal 170 contracts substantially straight, and excessive deflection and bending of the over tube 150 are eliminated. When the over tube 150 is drawn in, both the first balloon 130 and the second balloon 160 are caught in the intestinal canal 170, but the friction resistance of the first balloon 130 is smaller than the friction resistance of the second balloon 160. Therefore, even if the first balloon 130 and the second balloon 160 move to separate from each other, the first balloon 130 with small friction resistance slides with respect to the intestinal canal 170, and therefore, it does not happen that the intestinal canal 170 is damaged by being pulled by both the balloons 130 and 160.

Next, as shown in FIG. 15H, air is sucked from the first balloon 130 to deflate the first balloon 130. Then, the tip end part 136 of the insertion section 112 is inserted into as deep a part of the intestinal canal 170 as possible. Namely, the insertion operation as shown in FIG. 15C is performed again. Thereby, the tip end part 136 of the insertion section 112 can be inserted into a deep part of the intestinal canal 170. When the insertion section 112 is further inserted into a deep part, the pushing operation as shown in FIG. 15E is performed after the fixing operation as shown in FIG. 15D is performed, and the gripping operation as shown in FIG. 15F, the drawing-in operation as shown in FIG. 15G, and the inserting operation as shown in FIG. 15H are repeatedly performed in sequence. Thus, the insertion section 112 can be further inserted into a deep part of the intestinal canal 170.

During such an operation by the endoscope apparatus, the body fluid flowing backward from the gap between the over tube 150 and the insertion section 112 flows into the accordion-shaped extendable and contractible member 152 attached in the watertight state to the base end portion of the over tube 150. The base end portion of the accordion-shaped extendable and contractible member 152 is fitted onto the fold prevention part 117 in the watertight state via the ring-shaped fitting member 155 and the packing 159, and therefore, the body fluid does not leak out of the base end portion of the accordion-shaped extendable and contractible member 152. Thereby, leakage of the body fluid flowing backward from the inside of the intestinal canal can be prevented. The accordion-shaped extendable and contractible member 152 extends and contracts in its axial direction, namely, in the inserting direction of the over tube 150 and the insertion section 112, and therefore, the inserting operation and the drawing-in operation of the over tube 150 and the insertion section 112 can be performed smoothly.

Further, according to the over tube 150, the accordion-shaped extendable and contractible member 152 is formed to have the length such that the tip end part 158 of the over tube 150 does not contact the first balloon 130 when the accordion-shaped extendable and contractible member 152 is extended most as shown in FIG. 14A. As a result, at the stroke end at the time of insertion of the over tube 150 shown in FIG. 14A, breakage of the first balloon 130 due to contact/abutment of the tip end part 158 of the over tube 150 can be prevented.

In the embodiment, the accordion-shaped extendable and contractible member 152 with the extending and contracting direction having directivity in one direction is explained, but the form of the member does not matter if only the member is extendable and contractible. For example, as shown in FIGS. 16A and 16B, a bag-shaped member 180 having no directivity in the extending and contracting direction as an extending and contracting member can be applied. In this case, a restraining linear element 182 such as a wire and a string which restrains the most extended amount of the bag-shaped member 180 is attached to the bag-shaped member 180 so that the tip end 158 of the over tube 150 does not contact the first balloon 130 at the most extended time.

Namely, the bag-shaped member 180 is formed into a cylindrical shape with its both ends opened, and ring-shaped linear element support members 184 and 186 are fixed to the openings at both ends, and both end portions of a plurality of linear elements 182, 182 . . . are fixed to these linear element support members 184 and 186. The linear element 182 is formed to have such length as to prevent the tip end 158 of the over tube 150 from contacting the first balloon 130 when the linear element 182 is extended most (the most extended time) as in FIG. 16A. The linear element support member 184 is fixed to the base end portion of the tube body 151, and the linear element supporting member 186 is fixed to the ring-shaped fitting member 155. Reference character A in FIGS. 16A and 16B designates the difference between the most extended time and the most contracted time of the bag-shaped member 180, and reference character B designates a necessary moving amount at the time of operation of the endoscope. Reference character C designates a space between the tip end 158 of the over tube 150 and the first balloon 130 when the bag-shaped member 180 is contracted most.

FIGS. 17A and 17B show an example in which a drain port 188 is provided at the base end portion side of the accordion-shaped extendable and contractible member 152. This drain port 188 is provided at a rigid pipe body 190 so that the drain port 188 is not crushed when the accordion-shaped extendable and contractible member 152 is contracted. The base end portion of the accordion-shaped extendable and contractible member 152 is fixed to this pipe body 190, whereby the drain port 188 is provided to penetrate the base end portion of the accordion-shaped extendable and contractible member 152. This pipe body 190 is fixed to the ring-shape fitting member 155.

According to the over tube 150 having the drain port 188 like this, by connecting a suction pump 192 to the drain port 188, the body fluid which is stored in a gap between the accordion-shape extendable and contractible member 152 and the insertion section 112 can be discharged outside from the gap by the suction pump 192. Instead of using the pump 192, the body fluid stored in the gap can be discharged outside from the drain port 188 by pumping action which occurs at the time of contraction of the accordion-shaped extendable and contractible member 152.

Figure 18:
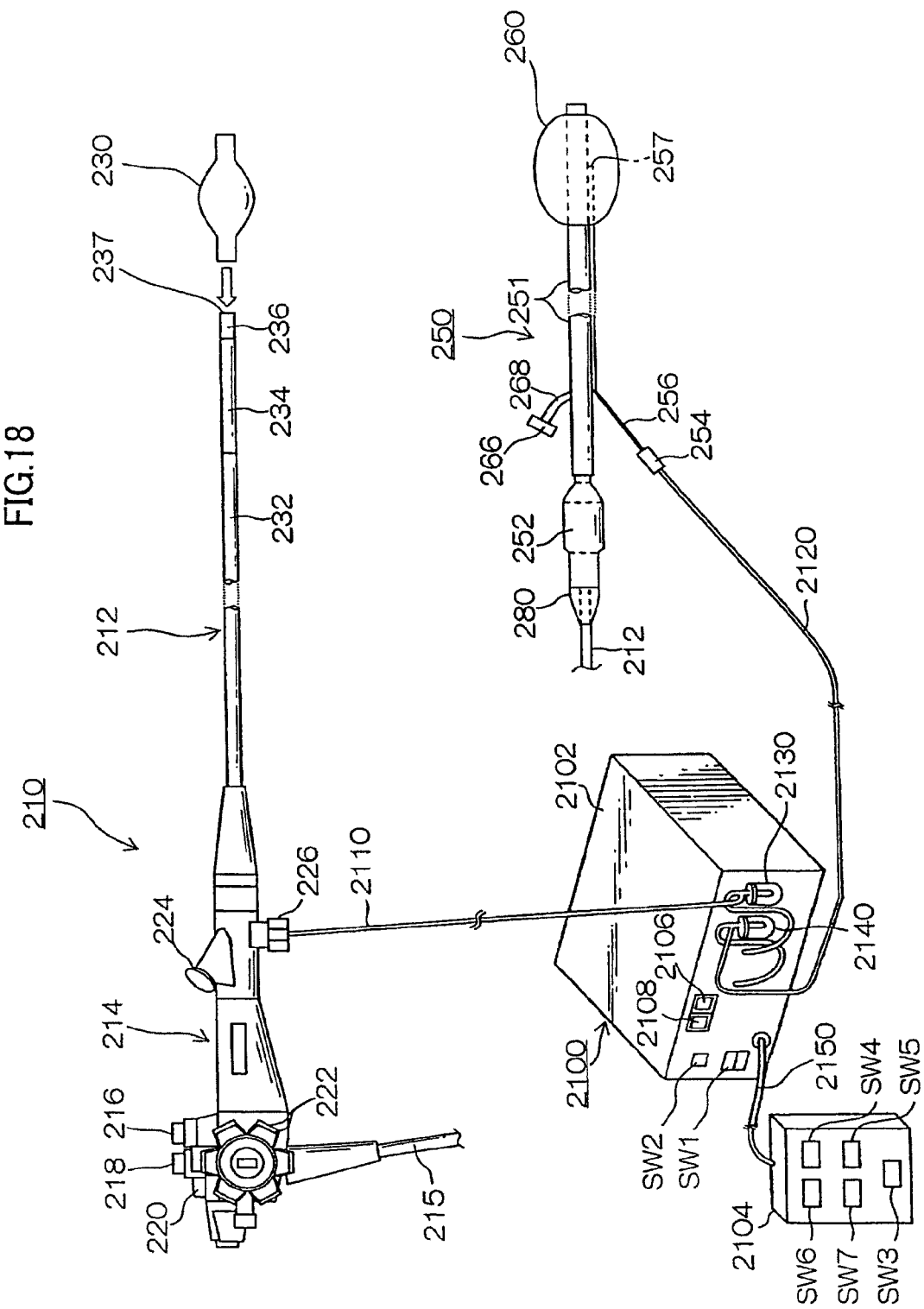
FIG. 18 is a system schematic diagram of an endoscope apparatus according to the present invention.

FIG. 18 shows a system schematic diagram of an endoscope apparatus to which an insertion assisting tool according to the present invention is applied. The endoscope apparatus shown in the drawing is constructed by an endoscope 210, an over tube (corresponding to the insertion assisting tool) 250, and a balloon control device 2100.

The endoscope 210 includes a hand operation section 214, and an insertion section 212 connected to the hand operation section 214. A universal cable 215 is connected to the hand operation section 214, and a connecter (not shown) connected to a processor and a light source device not shown is provided at a tip end of the universal cable 215.

On the hand operation section 214, an air/water passing button 216, a suction button 218, and a shutter button 220 which are operated by an operator are provided in parallel, and a pair of angle knobs 222 and 222, and a forceps insertion section 224 are provided at the respective positions. Further, the hand operation section 214 is provided with a balloon air port 226 for supplying air to a first balloon 230 and sucking air from the balloon 230.

The insertion section 212 is constructed by a flexible part 232, a curving part 234 and a tip end part 236. The curving part 234 is constructed by connecting a plurality of node rings to be able to curve, and is remotely operated to curve by the rotational operation of a pair of angle knobs 222 and 222 provided on the hand operation section 214. Thereby, a tip end surface 237 of the tip end part 236 can be directed in a desired direction.

Figure 19:
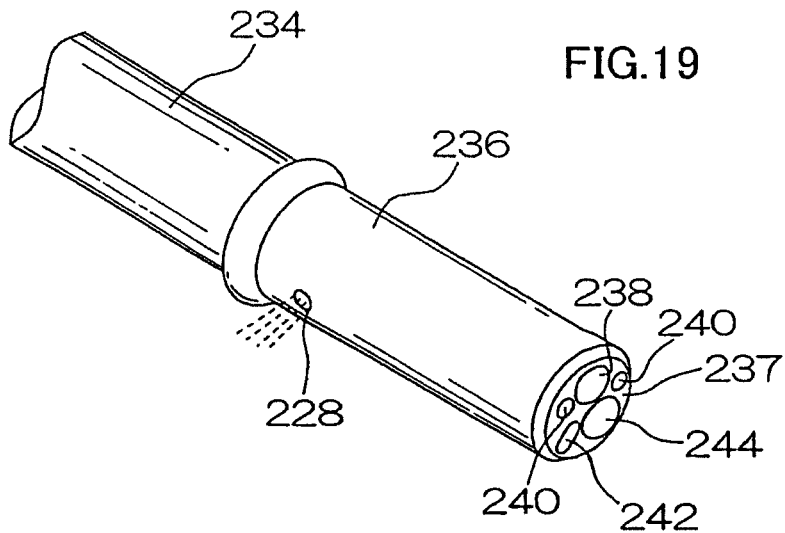
FIG. 19 is a perspective view showing the tip end part of the insertion section of the endoscope.

As shown in FIG. 19, the tip end surface 237 of the tip end part 236 is provided with an object optical system 238, an illumination lens 240, an air/water passing nozzle 242, a forceps port 244 and the like in predetermined positions. An air supply/suction port 228 is provided on an outer peripheral surface of the tip end part 236, and this air supply/suction port 228 communicates with the balloon air port 226 in FIG. 18 via an air supply tube (not shown) with an inner diameter of about 0.8 mm which is inserted through the insertion section 212. Accordingly, air is blown out of the air supply/suction port 228 of the tip end part 236 by supplying air into the balloon air port 226, and on the other hand, air is sucked from the air supply/suction port 228 by sucking air from the balloon air port 226.

Figure 20:
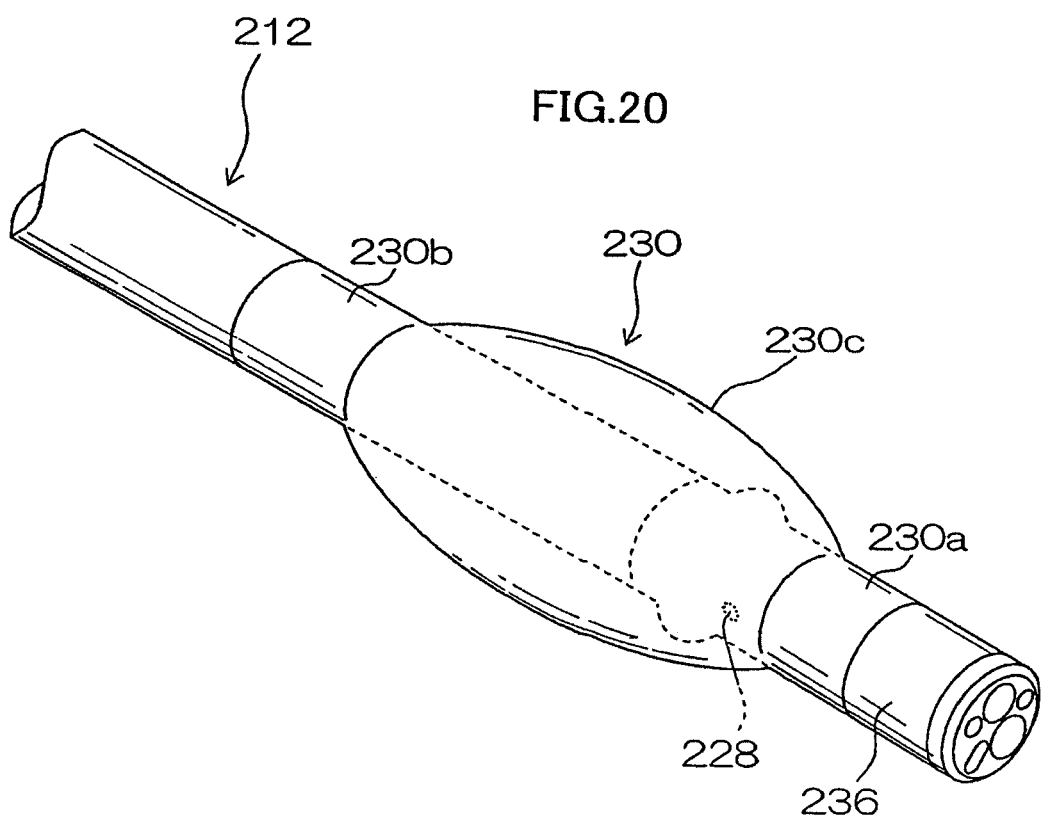
FIG. 20 is a perspective view showing the tip end part of the insertion section of the endoscope.

As shown in FIG. 18, the first balloon 230 constituted of an elastic body such as rubber is detachably attached to the tip end part 236 of the insertion section 212. The first balloon 230 is formed by a bulging portion 230c in a center and attaching portions 230a and 230b at both ends of the bulging portion 230c, and is attached to the tip end part 236 side so that the air supply/suction port 228 is located inside the bulging portion 230c as shown in FIG. 20. The attaching portions 230a and 230b are formed to have smaller diameters than the diameter of the tip end part 236, and after being closely fitted onto the tip end part 236 with their elastic forces, the attaching portions 230a and 230b are fixed with threads not shown wound around the attaching portions 230a and 230b. The fixation is not limited to the thread winding fixation, but the attaching portions 230a and 230b may be fixed to the tip end part 236 by fitting fixing rings onto the attaching portions 230a and 230b.

The first balloon 230 fitted onto the tip end part 236 has its bulging portion 230c inflated into a substantially spherical shape by blowing air from the air supply/suction port 228 shown in FIG. 19. On the other hand, by sucking air from the air supply/suction port 228, the bulging portion 230c is deflated and is closely fitted onto the outer peripheral surface of the tip end part 236.

Figure 21:
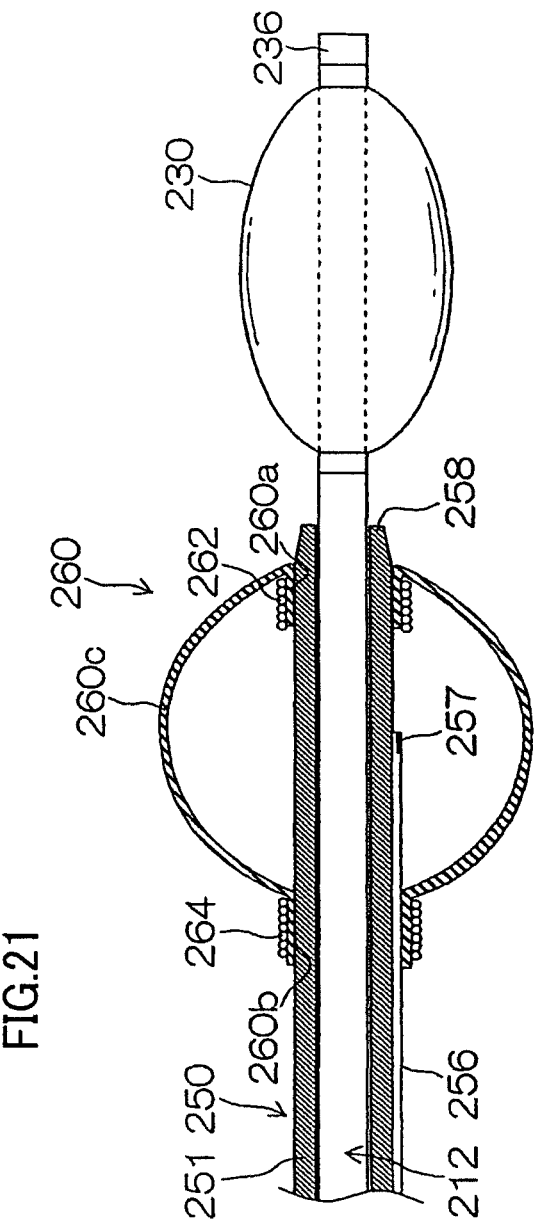
FIG. 21 is a sectional side view showing the over tube.
Figure 22:
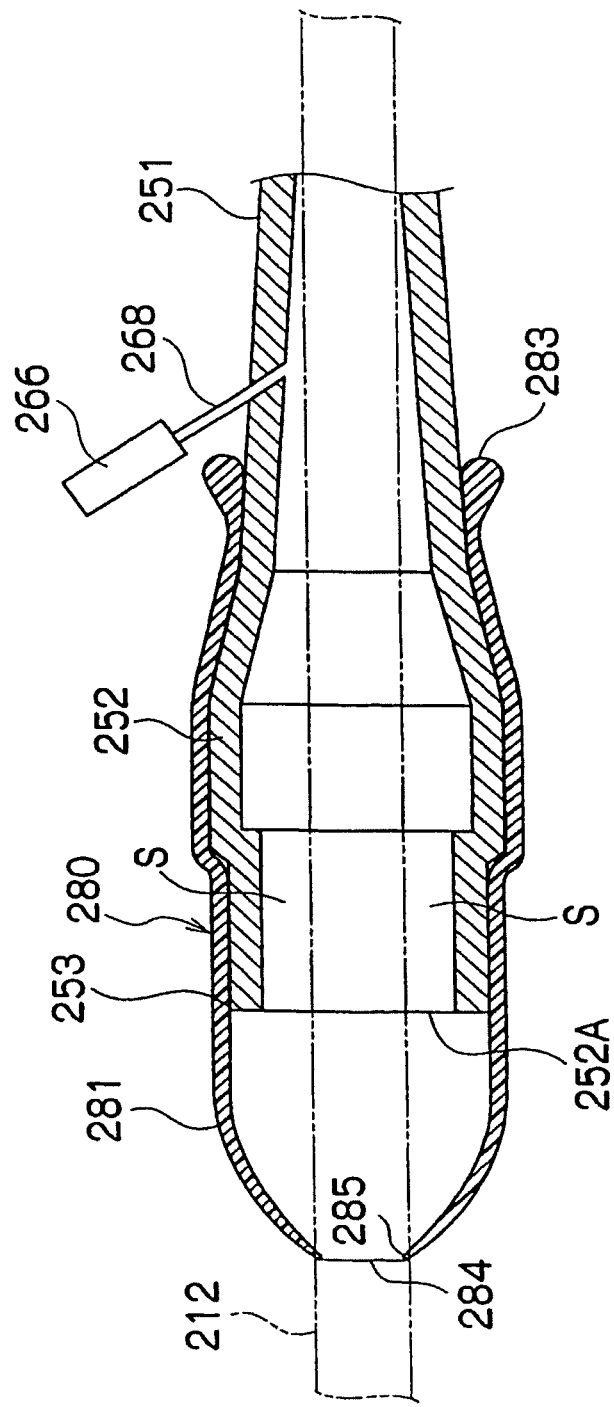
FIG. 22 is a sectional view of a tube attached to the gripping part of the over tube.

The over tube 250 shown in FIG. 18 is formed by a tube body 251, and a gripping part 252 to which a tube 280 having the function of a check valve is fitted. The tube body 251 is formed into a cylindrical shape and has a slightly larger inner diameter than an outer diameter of the insertion section 212, as shown in FIG. 21. The tube body 251 is constructed by covering an outer side of a flexible resin tube made of urethane or the like with lubricating coat and covering an inner side with the lubricating coat. The insertion section 212 is inserted toward the tube body 251 from the base end opening 252A of the gripping part 252 as shown in FIG. 22.

As shown in FIG. 18, a balloon air port 254 is provided at the base end side of the tube body 251. An air supply tube 256 with an inner diameter of about 1 mm is connected to the balloon air port 254, and this tube 256 is bonded to an outer peripheral surface of the tube body 251 and is provided to extend to a tip end portion of the tube body 251.

A tip end 258 of the tube body 251 is formed into a tapered shape. A second balloon 260 constituted of an elastic body such as rubber is fitted onto the base end side of the tip end 258 of the tube body 251. The second balloon 260 is fitted in the state in which the tube body 251 penetrates through the balloon 260, and is constructed by a bulging portion 260c in a center, and attaching portions 260a and 260b at both ends of the bulging portion 260c as shown in FIG. 21. The attaching portion 260a at the tip end side is folded back to the inside of the bulging portion 260c, and the attaching portion 260a that is folded back is fixed to the tube body 251 with an X-ray contrast thread 262 wound around the attaching portion 260a that is folded back. The attaching portion 260b at the base end side is disposed outside the second balloon 260, and is fixed to the tube body 251 with a thread 264 wound around the attaching portion 260b.

The bulging portion 260c is formed into a substantially spherical shape in a natural state (the state in which the bulging portion 260c does not inflate or deflate), and as for the size, the bulging portion 260c is formed to be larger than the size of the first balloon 230 in a natural state (the state in which the balloon 230 does not inflate or deflate). Accordingly, when the air is supplied to the first balloon 230 and the second balloon 260 at the same pressure, the outer diameter of the bulging portion 260c of the second balloon becomes larger than the outer diameter of the bulging portion 230c of the first balloon 230. The outer diameter of the second balloon 260 is constructed to be φ50 mm when the outer diameter of the first balloon 230 is φ25 mm, for example.

The aforementioned tube 256 is opened in the inside of the bulging portion 260c, where an air supply/suction port 257 is formed. Accordingly, when air is supplied from the balloon air port 254, the air is blown from the air supply/suction port 257, and thereby, the bulging portion 260c is inflated. When air is sucked from the balloon air port 254, the air is sucked from the air supply/suction portion 257, and the second balloon 260 is deflated. Reference numeral 266 in FIG. 22 designates an inlet port for filling a lubricating liquid such as water into the tube body 251, and the inlet port 266 communicates with the base end portion side of the tube body 251 via a tube 268 with a thin diameter.

Figure 23:
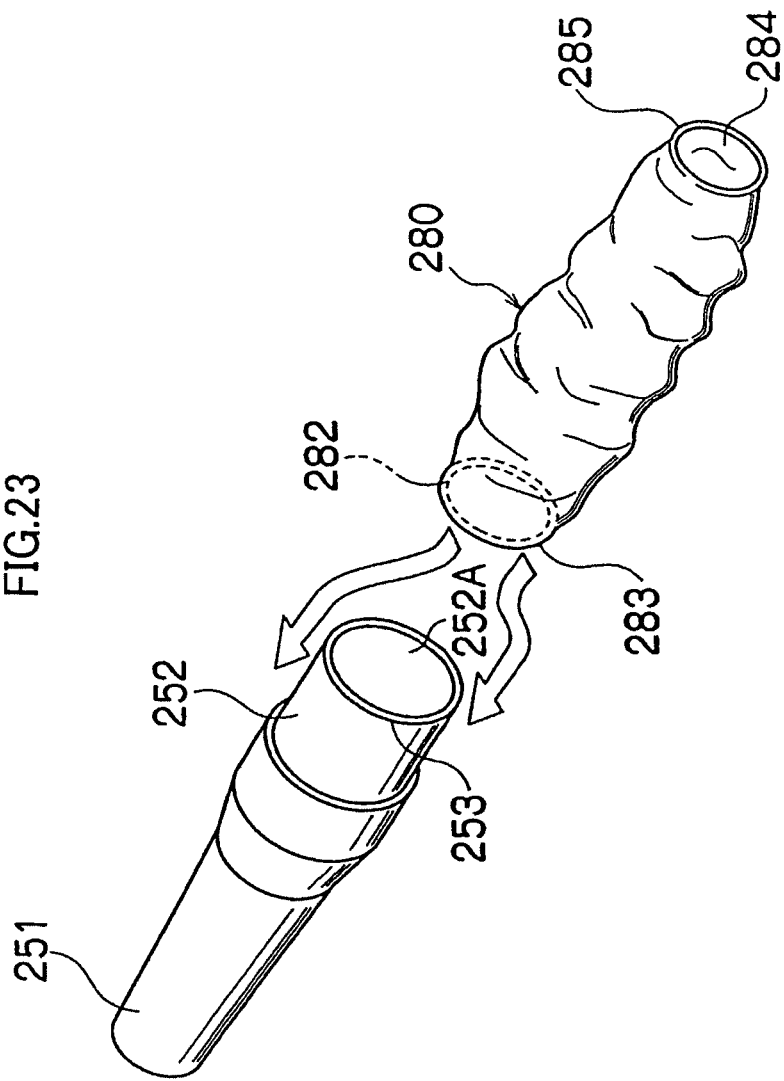
FIG. 23 is a perspective view of the over tube and the tube.

Incidentally, the tube 280 shown in FIG. 22 is formed into a substantially cylindrical shape by an elastic body such as natural rubber or synthetic rubber. Among openings at both ends of the tube 280, an opening 282 fitted onto the gripping part (the base end portion, at the side of the hand operation section, of the insertion assisting tool) 252 is formed to be smaller than the outer diameter of the base end part 253 of the gripping part 252. As a result, the tube 280 is fitted onto the gripping part 252 in the state in which the opening 282 is expanded in diameter with the elastic force as shown in FIG. 23. Namely, an edge portion 283 of the opening 282 of the tube 280 is closely fitted onto an outer surface of the gripping part 252 with the elastic force.

Figure 24A:
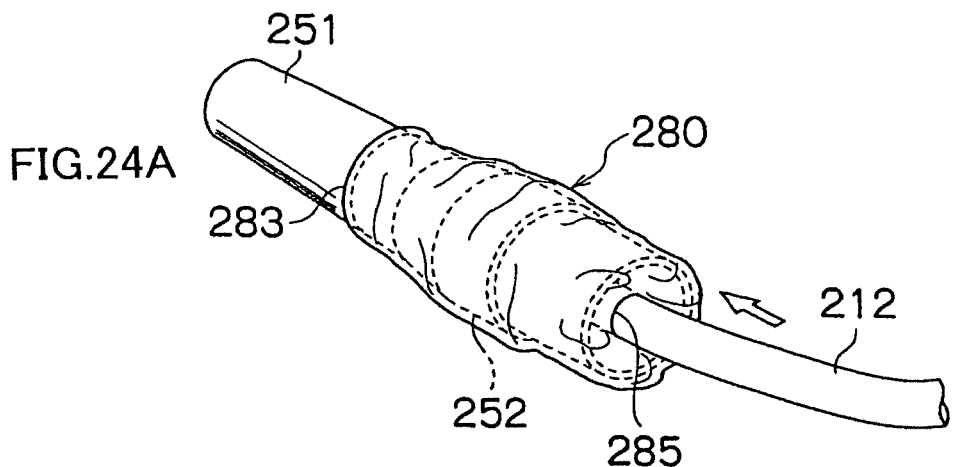
FIGS. 24A to 24C are explanatory views showing insertion and extraction operation of the insertion section with respect to the tube.

Among the openings at the both ends of the tube 280, an opening 284 which is fitted onto an outer surface of the insertion section 212 is formed to be smaller than the diameter of the insertion section 212 as shown in FIG. 22. The insertion section 212 is pushed into this opening 284 with the tip end part 236 inserted first as shown in FIG. 24A, whereby an edge portion 285 of the opening 284 is extended in diameter with the elasticity and closely fitted onto the insertion section 212. The diameter of the opening 284 of the tube is set at 70% to 90% of the outer diameter of the insertion section 212. Thereby, the insertion section 212 is closely fitted to the edge portion 285 of the opening 284 with the elasticity and inserted through the opening 284 slidably with respect to the opening 284.

Meanwhile, the balloon control device 2100 in FIG. 18 is the device which supplies and sucks fluid such as air to and from the first balloon 230, and supplies and sucks fluid such as air to and from the second balloon 260. The balloon control device 2100 is constructed by a device body 2102 including a pump, a sequencer and the like not shown, and a hand switch 2104 for remote control.

A front panel of the device body 2102 is provided with a power supply switch SW1, a stop switch SW2, a pressure gauge 2106 for the first balloon 230 and a pressure gauge 2108 for the second balloon 260. A tube 2110 for supplying/sucking air to and from the first balloon 230, and a tube 2120 for supplying/sucking air to and from the second balloon 260 are attached to the front panel of the device body 2102. Liquid storing tanks 2130 and 2140 for storing body fluid, which flows backward from the first balloon 230 and the second balloon 260 when the first balloon 230 and the second balloon 260 are broken, are respectively provided at midpoints of the respective tubes 2110 and 2120.

Meanwhile, the hand switch 2104 is provided with a similar stop switch SW3 to the stop switch SW2 at the side of the device body 2102, an ON/OFF switch SW4 for supporting pressurization/decompression of the first balloon 230, a pose switch SW5 for keeping the pressure of the first balloon 230, an ON/OFF switch SW6 for supporting pressurization/decompression of the second balloon 260, and a pose switch SW7 for keeping the pressure of the second balloon 260. This hand switch 2104 is electrically connected to the device body 2102 via a cable 2150.

The balloon control device 2100 which is constructed as above supplies air to the first balloon 230 and the second balloon 260 and inflates the first balloon 230 and the second balloon 260, and controls the air pressure at a fixed value to keep the first balloon 230 and the second balloon 260 in the inflated state. The balloon control device 2100 sucks air from the first balloon 230 and the second balloon 260 and deflates the first balloon 230 and the second balloon 260, and controls the air pressure at a fixed value to keep the first balloon 230 and the second balloon 260 in the deflated state.

Next, an operation method of the endoscope apparatus will be explained in accordance with FIGS. 25A to 25H.

First, as shown in FIG. 25A, the insertion section 212 is inserted into an intestinal canal (for example, descending limb of duodenum) 270 in the state in which the over tube 250 covers the insertion section 212. At this time, the first balloon 230 and the second balloon 260 are deflated.

Next, as shown in FIG. 25B, in the state in which the tip end 258 of the over tube 250 is inserted up to a bent portion of the intestinal canal 270, air is supplied to the second balloon 260 to inflate the second balloon 260. As a result, the second balloon 260 is caught in the intestinal canal 270, and the tip end 258 of the over tube 250 is fixed to the intestinal canal 270.

Next, as shown in FIG. 25C, only the insertion section 212 of the endoscope 210 is inserted into a deep part of the intestinal canal 270. Then, as shown in FIG. 25D, air is supplied to the first balloon 230 to inflate the first balloon 230. As a result, the first balloon 230 is fixed to the intestinal canal 270. In this case, the first balloon 230 is smaller in size at the time of inflation than the second balloon 260, and therefore, the burden exerted on the intestinal canal 270 is small, thus making it possible to prevent damage to the intestinal canal 270.

Next, after air is sucked from the second balloon 260 to deflate the second balloon 260, the over tube 250 is pushed in, and inserted along the insertion section 212, as shown in FIG. 25E. Then, after the tip end 258 of the over tube 250 is pushed into the vicinity of the first balloon 230, air is supplied to the second balloon 260 to inflate the second balloon 260 as shown in FIG. 25F. As a result, the second balloon 260 is fixed to the intestinal canal 270. Namely, the intestinal canal 270 is gripped by the second balloon 260.

Next, as shown in FIG. 25G, the over tube 250 is drawn in. Thereby, the intestinal canal 270 contracts substantially straight, and excessive deflection and bending of the over tube 250 are eliminated. When the over tube 250 is drawn in, both the first balloon 230 and the second balloon 260 are caught in the intestinal canal 270, but the friction resistance of the first balloon 230 is smaller than the friction resistance of the second balloon 260. Therefore, even if the first balloon 230 and the second balloon 260 move to separate from each other, the first balloon 230 with small friction resistance slides with respect to the intestinal canal 270, and therefore, it does not happen that the intestinal canal 270 is damaged by being pulled by both the balloons 230 and 260.

Next, as shown in FIG. 25H, air is sucked from the first balloon 230 to deflate the first balloon 230. Then, the tip end part 236 of the insertion section 212 is inserted into as deep a part of the intestinal canal 270 as possible. Namely, the insertion operation as shown in FIG. 25C is performed again. Thereby, the tip end part 236 of the insertion section 212 can be inserted into a deep part of the intestinal canal 270. When the insertion section 212 is further inserted into a deep part, the pushing operation as shown in FIG. 25E is performed after the fixing operation as shown in FIG. 25D is performed, the gripping operation as shown in FIG. 25F and the drawing-in operation as shown in FIG. 25G, and the inserting operation as shown in FIG. 25H are repeatedly performed in sequence. Thus, the insertion section 212 can be further inserted into the deep part of the intestinal canal 270.

During such an operation, the body fluid which flows backward from the gap between the tube body 251 of the over tube 250 and the insertion section 212 (see FIG. 21) due to internal pressure of the intestinal canal 270 is stored in the tube 280 without leaking out of the tube 280 because the edge portion 283 of the opening 282 of the tube 280 is attached to be closely fitted onto the gripping part 252 by the elastic force and the edge portion 285 of the opening 284 of the tube 280 is attached to be closely fitted onto the insertion section 212 by the elastic force as shown in FIG. 24A, and thus, the tube 280 exhibits the function of the check valve. As a result, leakage of the body fluid can be prevented.

In order to improve slip property of the insertion section 212 with respect to the over tube 250, in the over tube 250 shown in FIG. 18, a lubricating liquid is supplied to the over tube 250 from the inlet port 266 via the tube 268. By storing the lubricating liquid in the tube 280 and allowing the tube 280 have the pot function, it is made possible to fill the lubricating liquid in the gap between the over tube 250 and the insertion section 212. As a result, favorable slip property can be always obtained. Further, by the lubricating liquid pot function of the tube 280, the supply amount and the number of times of supply of the lubricating liquid from the inlet port 266 can be reduced.

Incidentally, in the endoscope apparatus including the over tube 250, the insertion section 212 is inserted into the base end portion of the gripping part 252 with some degree of freedom with respect to the base end portion as shown in FIG. 22 in consideration of operability of insertion and extraction of the insertion section 212 with respect to the over tube 250. Namely, a space S between the gripping part 252 and the insertion section 212 is set to be comparatively larger than spaces at the other positions, and insertion and extraction operability of the operator is enhanced by making the insertion and extraction direction of the insertion section 212 properly changeable by using the space S. Accordingly, in the case where the tube 280 is fitted onto the insertion section 212, it is also necessary to keep the insertion and extraction operability.

Figure 26:
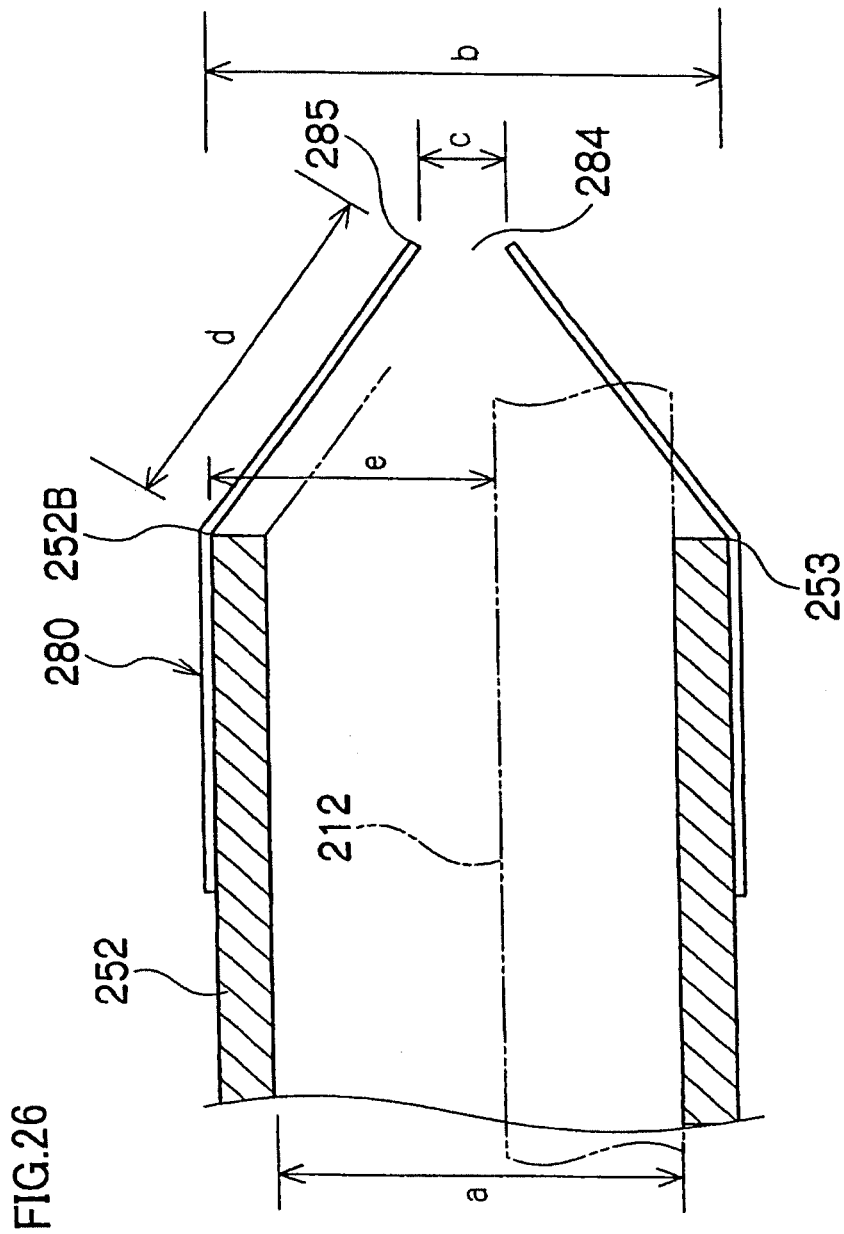
FIG. 26 is a schematic diagram for explaining the size of the tube.

Thus, the tube 280 of this embodiment is formed in the size which satisfies the formula d>a−c+(b−a)/2, where the inner diameter of the gripping part 252 of the over tube 250 is a, the maximum diameter of the tube 280 when the tube 280 is attached to the gripping part 252 (the outer diameter of the base end part 253 of the gripping part 252) is b, the diameter of the opening 284 of the tube 280 is c, and the shortest distance from the fixed portion B of the tube 280 to the gripping part 252 to the edge portion 285 of the opening 284 of the tube 280 is d as shown in FIG. 26. Namely, as shown by the chain double-dashed line in FIG. 26, the distance d is set to be longer than the distance e which is from the fixed portion 252B to the insertion section 212 when the insertion section 212 is put aside as much as possible by using the space S (see FIG. 22).

Figure 24B:
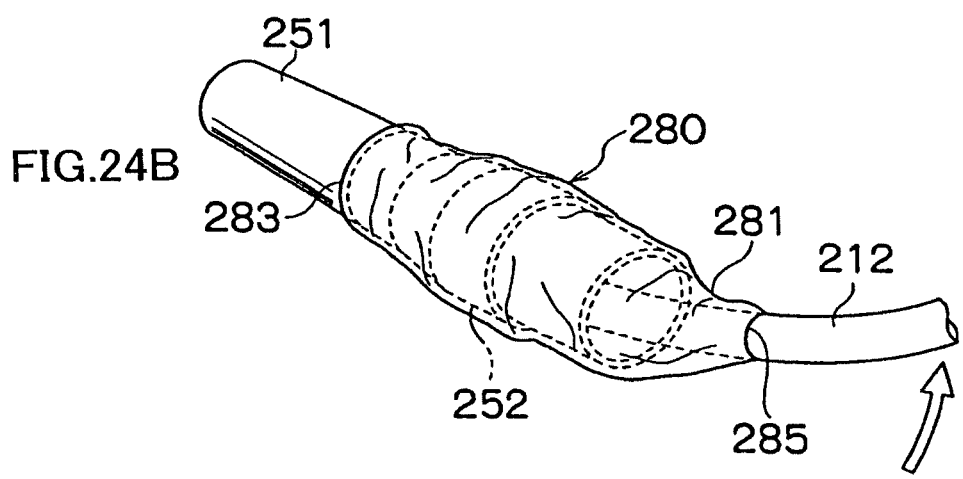
Figure 24C:
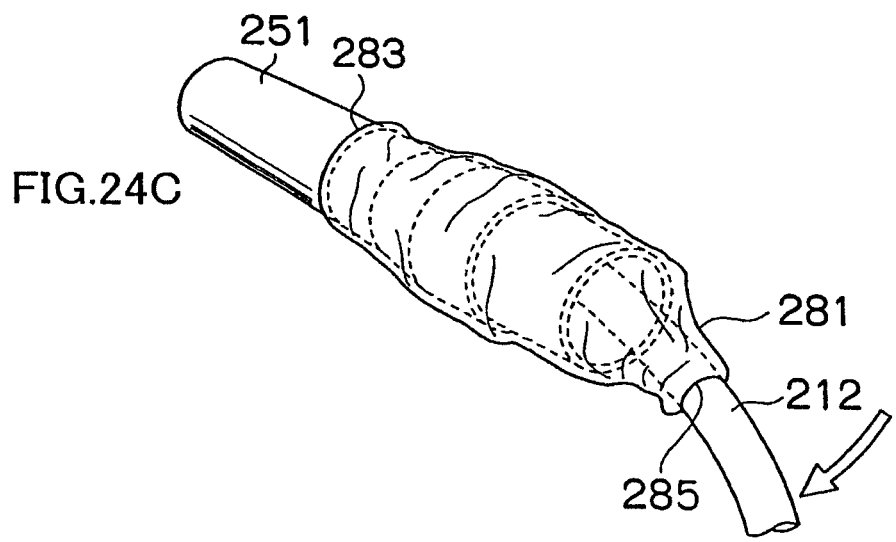

As a result, even when the insertion section 212 is put aside as much as possible by using the space S, slackness occurring to a circular conical portion 281 (see FIG. 22) which is the length d portion of the tube 280 does not disappear. Therefore, at the time of insertion and extraction operation using the space S of the tube 280 as shown in FIGS. 24B and 24C, the insertion section 212 does not receive any compelling force from the circular conical portion 281, and therefore, insertion and extraction operability can be maintained.

In the embodiment, the over tube which is used for inspection of a small intestine is explained as the insertion assisting tool, but the present invention is not limited to this, and tube 280 may be fitted onto a sliding tube which is used for inspection of a large intestine.

What is claimed is:

1. An insertion assisting tool for an endoscope into which an insertion section of the endoscope is inserted, comprising:
   a substantially cylindrical tube formed of an elastic body in which a smaller opening than a diameter of a base end part of the insertion assisting tool is formed at one end and a smaller opening than a diameter of the endoscope insertion section is formed at the other end,
   wherein in the tube, the opening formed at the one end is attached to the base end part of the insertion assisting tool in close contact with the base end part, the tube covers from outside of the insertion assisting tool an end portion of the base end part of the insertion assisting tool, and the insertion section is slidably inserted through the tube with the insertion section of the endoscope closely fitted in the opening formed at the other end, and
   wherein the tube is formed in a size which satisfies a formula of $d > a - c + (b-a)/2$ where an inner diameter of the insertion assisting tool is a, a maximum diameter of the tube when the tube is attached to the insertion assisting tool is b, a diameter of an opening formed at the other end of the tube is c, and a distance from a fixing portion of the tube to the insertion assisting tool to an edge portion of the opening formed at the other end of the tube is d.

2. The insertion assisting tool for an endoscope according to claim 1, further comprising: an inflatable and deflatable balloon attached to at least one of the insertion section of the endoscope and a tip end part of the insertion assisting tool.

3. The insertion assisting tool for an endoscope according to claim 1, wherein a diameter of the opening formed at the other end of the tube is set at 70% to 90% of outer diameter of the insertion section.

4. The insertion assisting tool for an endoscope according to claim 1, wherein a space between inner peripheral surface of the base end part of the insertion assisting tool and outer peripheral surface of the insertion section is set to be larger than spaces between inner peripheral surface of parts other than the base end part of the insertion assisting tool and outer peripheral surface of the insertion section.

5. The insertion assisting tool for an endoscope according to claim 1, wherein in a first state, the smaller opening at the base end part has the diameter smaller than the diameter of the base end part and in a second state, has a diameter larger than the diameter of the base end part such that the tube covers an end portion of the base end part of the insertion assisting tool.

* * * * *